United States Patent
Corless et al.

(10) Patent No.: US 9,772,226 B2
(45) Date of Patent: Sep. 26, 2017

(54) REFERENCED AND STABILIZED OPTICAL MEASUREMENT SYSTEM

(75) Inventors: John Douglas Corless, Dallas, TX (US); Andrew Weeks Kueny, Dallas, TX (US); Mark Anthony Meloni, The Colony, TX (US)

(73) Assignee: Verity Instruments, Inc., Carrollton, TX (US)

( * ) Notice: Subject to any disclaimer, the term of this patent is extended or adjusted under 35 U.S.C. 154(b) by 813 days.

(21) Appl. No.: 13/180,508

(22) Filed: Jul. 11, 2011

(65) Prior Publication Data

US 2013/0016343 A1    Jan. 17, 2013

(51) Int. Cl.
| | |
|---|---|
| *G01J 1/34* | (2006.01) |
| *G01J 1/00* | (2006.01) |
| *G01J 3/00* | (2006.01) |
| *G01J 3/02* | (2006.01) |
| *G01J 3/10* | (2006.01) |
| *G01J 3/42* | (2006.01) |
| *G01N 21/95* | (2006.01) |

(52) U.S. Cl.
CPC ............ *G01J 3/0218* (2013.01); *G01J 3/10* (2013.01); *G01J 3/42* (2013.01); *G01N 21/9501* (2013.01)

(58) Field of Classification Search
CPC .......... G01J 3/10; G01J 3/0205; G01J 3/0218; G01J 3/027; G01J 3/42; G01N 21/84; G01N 21/9501; G01N 2201/061; G01N 2201/0696; H05B 41/30

USPC ................ 356/217, 213, 300; 438/65, 69
See application file for complete search history.

(56) References Cited

U.S. PATENT DOCUMENTS

| | | | | |
|---|---|---|---|---|
| 6,459,425 | B1 * | 10/2002 | Holub | G01J 3/02 345/204 |
| 2006/0285108 | A1 * | 12/2006 | Morrisroe | F23C 99/003 356/316 |
| 2007/0013902 | A1 * | 1/2007 | Backhauss | G01N 21/9501 356/237.5 |
| 2008/0015802 | A1 * | 1/2008 | Urano | G01N 21/4738 702/81 |
| 2009/0103081 | A1 * | 4/2009 | Whelan | G01J 3/28 356/243.1 |

* cited by examiner

*Primary Examiner* — Sunghee Y Gray

(57) ABSTRACT

A referenced and stabilized optical measurement system includes a light source, a plurality of optical elements and optical fiber assemblies and a detector arranged to compensate for the effects of system variation which may affect measurement performance. A non-continuous light source provides a common source light on a common source path. A reference light and a measurement light are derived from the common source light and propagated across separate paths of optically matching optical components in order to produce a common signal variation on both the reference light signal and the measurement light signal. Light paths exposed to air are contained indiscrete volumes for purging gasses from the volumes. Ratios of the reference signal and measurement signal are acquired under various conditions for compensating the measurement signal for system variations.

18 Claims, 18 Drawing Sheets

REFERENCED AND STABILIZED OPTICAL MEASUREMENT SYSTEM

BACKGROUND

The present disclosure relates to optical measurement systems and methods of use. More particularly, the present invention is directed to an optical system for mitigating drift, fade and errors due to due to absorption and solarization effects in a flashlamp driven optical measurement system and detecting and correcting any remaining error.

Optical measurement systems are employed in a variety of industries, such as the semiconductor processing industry, for real-time monitoring of workpiece modification and process control. Optical measurement systems may be integrated with a semiconductor processing tool and utilized in-situ for real-time process control or may be used in-line for feedback control. Typically, monitored processes include semiconductor etching, deposition and CMP processes for film thickness and plasma monitoring applications.

Especially in the semiconductor processing industry, the use of increasingly thinner material layers and smaller features sizes, in accordance with Moore's Law, has led to a need to interrogate these small features with increasingly shorter wavelengths and tighter repeatability to achieve desired levels of measurement accuracy and precision. Shorter wavelengths of light in the UV and DUV regions of the spectrum (i.e., wavelengths less than 400 nm) cannot consistently be transmitted in optical fibers due to absorption and solarization effects. To utilize these short wavelengths for measurement, the use of optical fibers must be minimized or optical measurement systems must be alternatively free-space coupled. However, the removal of optical fibers or use of free-space coupling imposes considerable design challenges and limits the integrability of measurement systems.

FIG. 1 shows a pictorial schematic of a prior art optical measurement system 100. Optical measurement system 100 includes light analyzing device 110, light source 120, optical assembly 130, optical fiber assembly 140, computer 150 and workpiece 160. Light analyzing device 110 is commonly a spectrograph, spectrometer, monochromator or other light analyzing device providing wavelength discrimination. Light source 120 is either a continuous broadband emission source (e.g., tungsten halogen lamp or deuterium lamp) or a pulsed broadband emission source such as a xenon flashlamp. Optionally, narrowband continuous or pulsed emission sources such as lasers are used. Optical assembly 130 is designed to direct light of one or more wavelengths emitted from light source 120 onto workpiece 160 which is a silicon semiconductor wafer, sapphire substrate or other workpiece. Optical assembly 130 commonly acts to either focus or collimate light from light source 120 onto workpiece 160. Optical fiber assembly 140 is commonly a bifurcated optical fiber assembly which directs light from light source 120 to workpiece 160 via optical assembly 130 and subsequently directs light collected upon reflection from workpiece 160 via optical assembly 130 to light analyzing device 110. Computer 150 is used to control light analyzing device 110 and light source 120 and is also used to analyze data collected by light analyzing device 110. Computer 150 may also provide signals to control external systems such as processing tools (not shown).

UV and DUV radiation adversely affects light analyzing device 110, light source 120, optical assembly 130 and optical fiber assembly 140 such that analysis performed by computer 150 of reflected light signals from workpiece 160 will contain errors (e.g., drifts, variations, noise, signal fade) and result in misprocessing of workpieces. UV and DUV radiation exposure causes measurement errors as a result of solarization of optical fibers, degradation of measurement system elements, and absorption by oxygen and the creation of and absorption by ozone in the optical signal path. In addition to the effects of UV and DUV, optical measurement system 100 is subject to other sources of variation that contribute to measurement error and/or drift including detector variation, CCD aging, lamp variation, lamp aging and mechanical dis-alignment or variation.

BRIEF SUMMARY

An optical measurement system and method for operating are provided herein for mitigating system and signal errors and compensating the measurement signal for errors and system variations that cannot be eliminated. The optical measurement system addresses the absorption and solarization effects by purposely modifying specific components for each detriment. For instance, areas within the present optical system with air volumes where the light signals are exposed to oxygen and, thereby suffer from the creation of ozone and absorption, are purged and filled with an inert gas that is not vulnerable to absorption or the creation of compounds that may absorb portions of the light signal. These purgeable volumes are provided with inlet and exhaust gas ports for purging the volume there within. Optical components within the assemblies that are susceptible to solarization effects that can be eliminated from the system are omitted; others are constructed from low-solarization optical materials, in order to reduce solarization of the optics. For instance, fiber optic assemblies are eliminated from the system wherever possible. Those that must remain in the present optical system utilize a commercially available low-solarization optical fiber.

In accordance with still another exemplary embodiment of the present invention, light signals utilize common optical components wherever possible, thereby ensuring that signal variations due to optical components are common to the reference and measurement light signals. This characteristic is important as the source light signal will be split into a reference light signal and a measurement light signal. Since the reference light signal and a measurement light signal are derived from a common source light signal, any signal variation existent in the light signal path up to the point of splitting will be common to both the reference light signal and a measurement light signal. A reference signal path is created of low-solarization optical components that optically match the low-solarization optical components used in the measurement signal path of the optical system, each for receiving the source light with the common signal variation. In so doing, any additional signal variations occurring on the reference light signal will be matched on the measurement light signal (or common to both the reference and measurement light signals). The measurement light signal can then be compensated for light signal variations, measurement error and/or drift resulting from, for example, the short-term and long-term solarization effects, the presence of oxygen/ozone, detector variation, CCD aging, lamp variation and lamp aging, by ratioing the reference and measurement signals. The compensated measurement signal can then be used for evaluating the state of a production process on a wafer.

One exemplary method for compensating the measurement signal is by using the ratios of calibration reference and measurement signals for not only calibrating a current measurement signal but also for approximating a gain for compensating subsequent measurement signal variations. For example, the optical measurement system is calibrated to a dark calibration standard, a known calibration standard and to a sample workpiece. Prior to a production run, ratios of the reference and measurement signal from the dark calibration standard and the known calibration standard are collected and saved. Upon initiation of a production run of a workpiece, a ratio of an initial reference and measurement signal from the workpiece is collected and saved. Then, current reference and measurement signals are monitored during production and ratioed. Using these four ratios of the reference and measure signals, the current measurement can be compensated for system variations.

BRIEF DESCRIPTION OF THE SEVERAL VIEWS OF THE DRAWINGS

The novel features believed characteristic of the present invention are set forth in the appended claims. The invention itself, however, as well as a preferred mode of use, further objectives and advantages thereof, will be best understood by reference to the following detailed description of an illustrative embodiment when read in conjunction with the accompanying drawings wherein:

Figure 1:
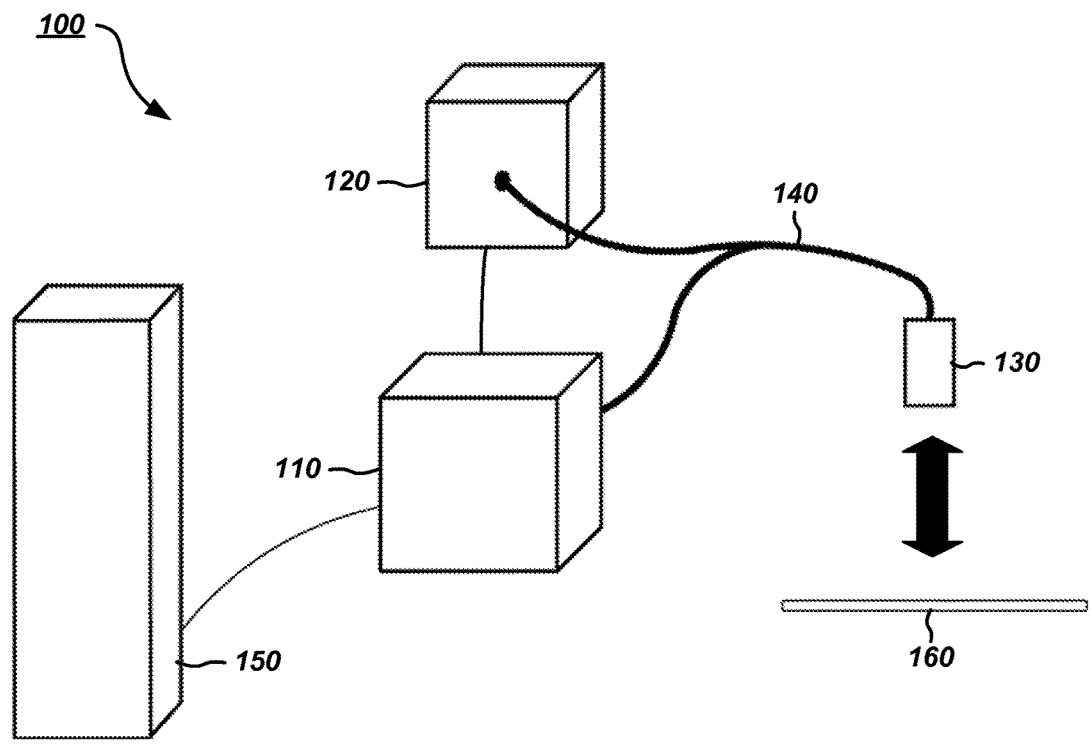
FIG. 1 is a pictorial schematic of a prior art optical measurement system.

Other features of the present invention will be apparent from the accompanying drawings and from the following detailed description. It is noted that, for purposes of illustrative clarity, certain elements in the drawings may not be drawn to scale.

DETAILED DESCRIPTION OF ILLUSTRATED EMBODIMENTS

| Element Reference Number Designations | |
|---|---|
| 100: | Optical measurement system |
| 110: | Light analyzing device |
| 120: | Light source |
| 130: | Optical assembly |
| 140: | Optical fiber assembly |
| 150: | Computer |
| 160: | Workpiece |
| 200: | Plot of relative signal change |
| 210: | Relative signal change below 200 nm |
| 220: | Relative signal change above 200 nm |
| 300: | Plot of long-term relative signal change |
| 310: | Relative signal change due to fiber solarization |
| 400: | Plot of transient relative signal change |
| 410: | Transient short-term solarization |
| 500: | Plot of shot-to-shot lamp signal variation |
| 510: | Shot-to-shot signal variation of lamp |
| 600: | Plot of CCD signal response variation |
| 610: | Signal response variation between multiple CCDs |
| 620: | Signal response variation in a single CCD |
| 700: | Optical measurement system |
| 710: | Flash illumination source |
| 712: | Source optical fiber assembly |
| 730: | Spectrograph |
| 750: | Optical assembly |
| 752: | Reference optical fiber assembly |
| 754: | Measurement optical fiber assembly |
| 780: | Workpiece interrogation light signal |
| 790: | Workpiece |
| 810: | Flash assembly |
| 815: | Flash assembly housing |
| 816: | Lamp |
| 818: | Source light signal |
| 820: | Flash assembly purged volume |
| 822: | Flash assembly containment housing |

-continued

Element Reference Number Designations

| | |
|---|---|
| 824: | Flash assembly purged volume inlet |
| 826: | Flash assembly purged volume exhaust |
| 830: | Spectrograph assembly |
| 834: | Spectrograph optics |
| 835: | Spectrograph assembly housing |
| 836-1: | First (reference) CCD detector channel |
| 836-2: | Second (measurement) CCD detector channel |
| 838-1: | First (reference) light signal |
| 838-2: | Second (measurement) light signal |
| 840: | Spectrograph purged volume |
| 842: | Spectrograph purged volume containment housing |
| 844: | Spectrograph purged volume inlet |
| 846: | Spectrograph purged volume exhaust |
| 850: | Optical assembly |
| 854: | Optics |
| 855: | Optical assembly housing |
| 860: | Optical assembly purged volume |
| 862: | Optical purged volume containment housing |
| 864: | Optical purged volume inlet |
| 866: | Optical purged volume exhaust |
| 910: | Flashlamp |
| 930: | Spectrograph |
| 1005: | Baseplate |
| 1007: | Main body |
| 1009: | Topplate |
| 1011: | Fiber retention fitting |
| 1013: | Fiber retention fitting |
| 1014: | Fiber retention fitting |
| 1015: | Gas fitting |
| 1017: | Purge passage |
| 1019: | Purge passage |
| 1021: | Purge passage |
| 1023: | cavity |
| 1025: | Light cone |
| 1031: | Beamsplitter |
| 1032: | Mirror |
| 1035: | Off-axis parabolic mirror |
| 1038: | Mirror |
| 1050: | Optical assembly |
| 1105: | Baseplate |
| 1107: | Main body |
| 1109: | Topplate |
| 1110-1: | Miniature flash assembly |
| 1110-2: | flashlamp assembly |
| 1111: | Fiber retention fitting |
| 1115: | Gas fitting |
| 1117: | Purge passage |
| 1119: | Purge passage |
| 1121: | Purge passage |
| 1123: | cavity |
| 1125: | Light cone |
| 1131: | Beamsplitter |
| 1132: | Mirror |
| 1135: | Off-axis parabolic mirror |
| 1138: | Mirror |
| 1150: | Optical assembly |

Prior art systems such as optical measurement system 100 are subject to any/all of the above-mentioned error sources and have limited suitability for high repeatability and high accuracy optical measurements, which limits their functionality for in situ and/or inline applications. To overcome the shortcomings of prior art systems, the present invention generally includes a system and method for optical measurement which compensates for the deleterious effects of solarization and variable signal attenuation as well as compensating for other system drift and variation. Other advantages of the current invention will be described below in association with embodiments.

Essentially, the optical measurement system described below in accordance with exemplary embodiments of the present invention treat the absorption and solarization effects separately by purposely modifying specific components of the presently described optical measurement system for each detriment. For instance, areas within the present optical system with air volumes where the light signals that are exposed to oxygen and, thereby suffer from the creation of ozone and absorption in that optical signal path, are purged and filled with an inert gas that is not vulnerable to absorption or the creation of compounds that may absorb portions of the light signal. Additionally, these purged volumes are provided with inlet and exhaust gas ports for purging the volume there within. Additionally, optical components within the assemblies that are exposed to DUV and UV light are constructed from low-solarization optical materials, in order to further reduce solarization of the optical elements themselves. In addition, other assembly components that are susceptible to absorption and solarization effects are modified or eliminated in order to reduce those effects on the light signals. For instance, fiber optic assemblies are eliminated wherever possible. Those that remain in the present optical measurement system utilize commercially available low-solarization optical fiber. Finally, in accordance with still another exemplary embodiment of the present invention, a reference signal path is created of matched low-solarization optics that essentially duplicates the measurement signal path of the optical system. In so doing, the reference light signal can be monitored for changes indicative of both the short-term and long-term effects of the presence of oxygen/ozone, and solarization. For example, prior to any production runs, the optical system is calibrated, as is generally the practice, however, the intensity of the reference light signal is recorded across all wavelengths to be monitored. This calibration forms the baseline reference measurement that all other future reference light signals are compared to in order to detect and quantify any drift, fade or errors due to absorption and solarization effects within the system. Appropriate maintenance thresholds are established for the wavelength intensities, such that once one or any of the thresholds are crossed, which is usually brought about by the long-term effects of solarization and absorption, the optical system may be deactivated for maintenance and recalibration. More importantly, on any given measurement, if the reference signal differs at any wavelength from the value it had during the calibration step, it can be inferred that a similar change will have been imparted to the signal in the measurement signal path and that the change should be removed mathematically. Other improvements and advantages of the presently described invention will become apparent with the discussion of the description of the various exemplary aspects and embodiments.

In the following description, reference is made to the accompanying drawings that form a part hereof, and in which is show by way of illustration, specific embodiments in which the invention may be practiced. These embodiments are described in sufficient detail to enable those skilled in the art to practice the invention, and it is to be understood that other embodiments may be utilized. It is also to be understood that structural, procedural and system changes may be made without departing from the spirit and scope of the present invention. The following description is, therefore, not to be taken in a limiting sense. For clarity of exposition, like features shown in the accompanying drawings are indicated with like reference numerals and similar features as shown in alternate embodiments in the drawings are indicated with similar reference numerals.

Figure 2:
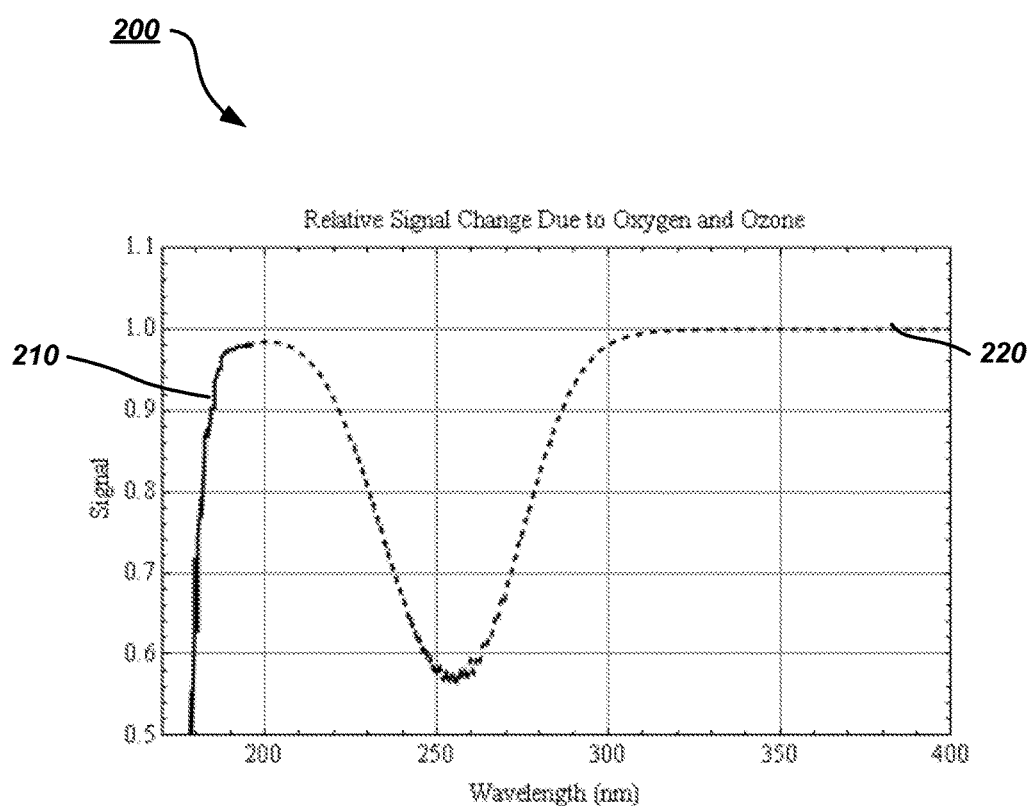
FIG. 2 is a plot of the relative signal change due to the absorption of light at various wavelengths caused by the presence of ozone and oxygen in the optical path, in accordance with an exemplary embodiment of the present invention.

FIG. 2 shows plot 200 of the relative signal change due to the absorption of light at various wavelengths caused by the presence of ozone and oxygen in an optical path of an optical measurement system. As shown by solid curve 210, oxygen readily absorbs light at wavelengths less than 200 nm and may provide signal attenuation at 180 nm of greater than 50% depending upon the oxygen concentration and optical path length. When pumped by UV light, oxygen is converted into ozone which as shown by dashed curve 220 has strong signal absorption near 250 nm. The conversion of oxygen into ozone and the decay of ozone into oxygen is a continuous process governed by creation and decay rate equations and are therefore time-varying. A short-term effect of the presence of oxygen/ozone is variable attenuation until equilibrium is achieved. A long-term effect is a possible high level of signal loss upon equilibrium of the creation/decay process. When present in optical measurement systems that utilize non-continuous illumination, such as described herein below, oxygen and ozone may provide optical signal level drift, fade and loss.

Figure 3:
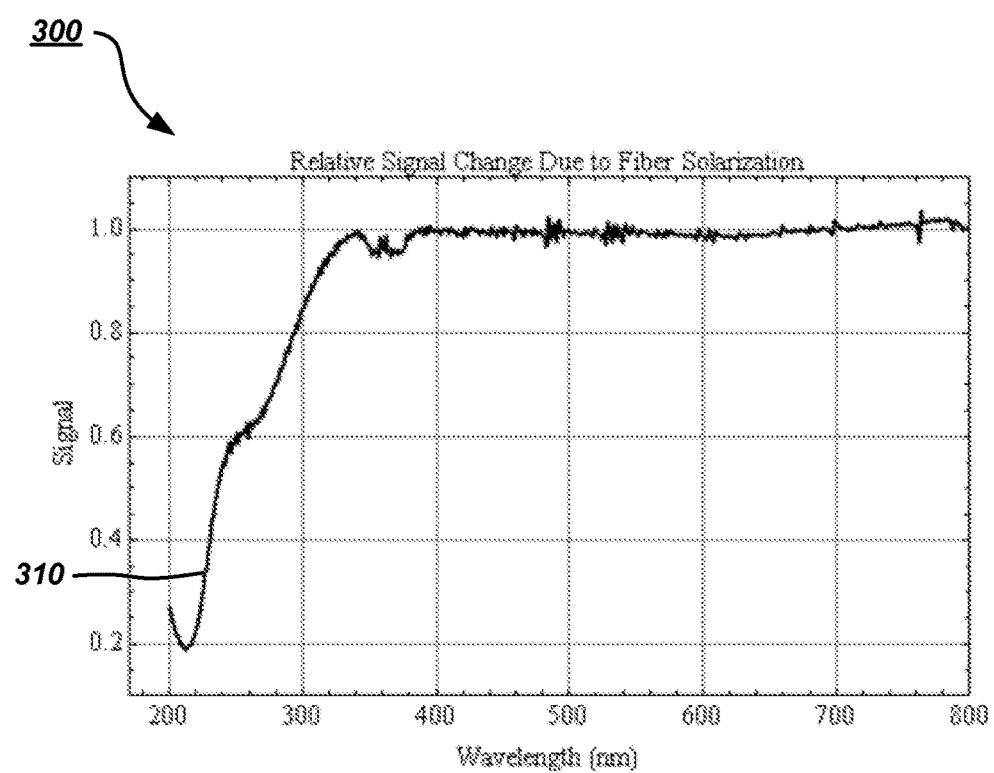
FIG. 3 is a plot of the long-term relative signal change in an optical fiber due to solarization of the optical fiber when exposed to UV and DUV radiation, in accordance with an exemplary embodiment of the present invention.

FIG. 3 shows plot 300 of the long-term relative signal change in an optical fiber due to solarization of the optical fiber when exposed to UV radiation from a xenon flashlamp. As shown by solid curve 310, long-term solarization may decrease transmission of an optical fiber by amounts as great as 80% at certain wavelengths. Long-term solarization often shows a continuous decrease in transmission with exposure until a final asymptotic value is reached. This exposure time may be multiple days or weeks, depending upon the incident light flux. This temporal variation is not suitable for a production environment, since signal drift will continuously occur during this period, and measurement errors may continuously change.

Figure 4:
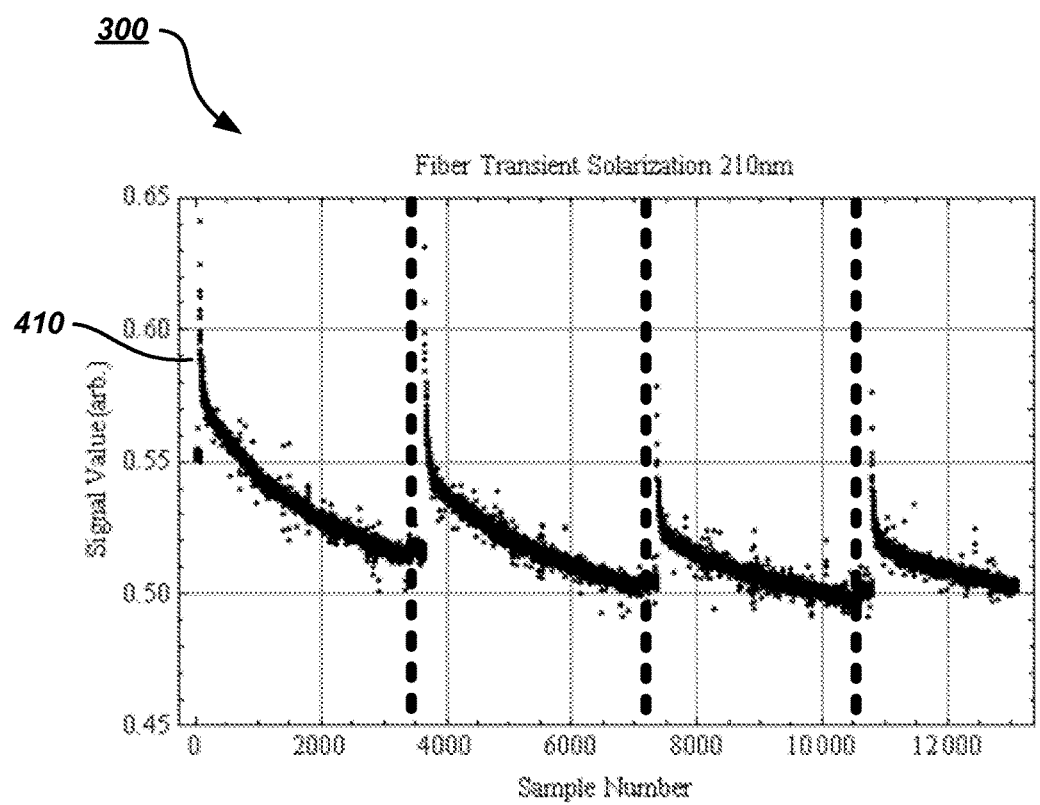
FIG. 4 is a plot of the transient relative signal change of an optical fiber caused by time-varying exposure of the optical fiber to UV and DUV radiation from a xenon flashlamp, in accordance with an exemplary embodiment of the present invention.

FIG. 4 shows plot 400 of the transient relative signal change of an optical fiber caused by time-varying exposure of the optical fiber to DUV and UV radiation from a xenon flashlamp. The data of plot 400 includes a series of four sets of measurements of solarization-induced attenuation each having approximately 3500 flashes of a xenon flashlamp in rapid succession followed by a time period when the xenon flashlamp is not flashed, such as between workpiece measurement cycles when workpieces may be exchanged in a process tool. Vertical dashed lines are used to separate each set of measurements. Each set of data correlates to data gathered during a time period approximating a single production cycle for a single wafer process. As shown by curve 410, short-term solarization poses an additional difficulty over long-term solarization in that the transmission partially may recover after an intermediate period of non-exposure that occurs subsequent to or between wafer processing cycles. This is a significant problem for common utilization of optical measurement systems in semiconductor processing applications, since processing does not occur 100% of the time but starts/stops on the time frame of a few minutes as workpieces are processed and then exchanged for subsequent workpieces and measurement is restarted. Long-term solarization drift may also be seen in FIG. 4 by observing that upon each subsequent set of 3500 flashes the signal level continues to drift lower.

Figure 5:
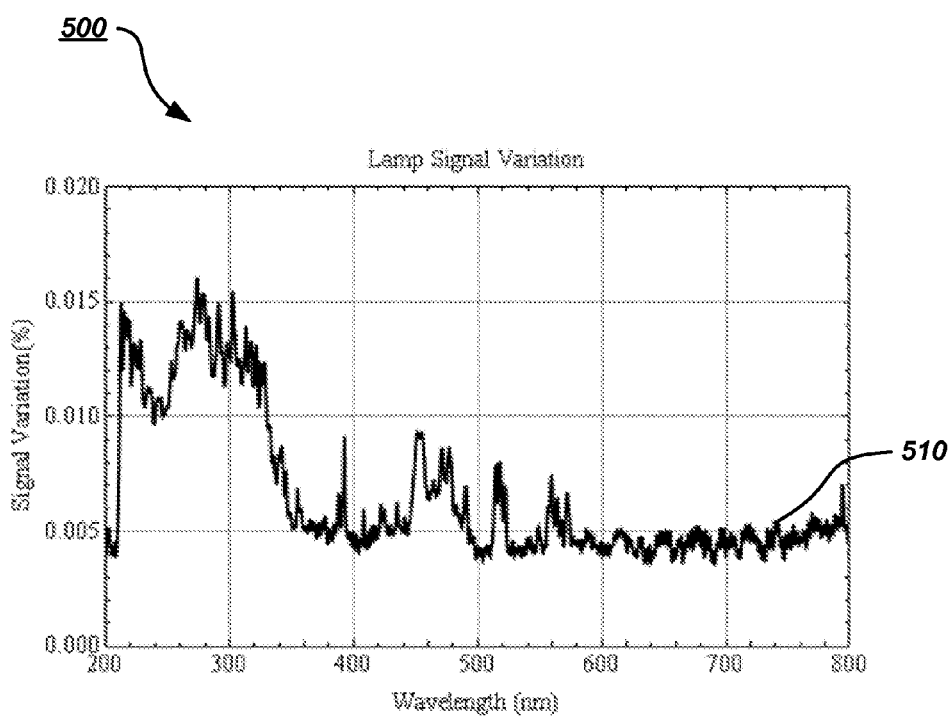
FIG. 5 is a plot of shot-to-shot signal variation of a xenon flashlamp plotted versus wavelength, in accordance with an exemplary embodiment of the present invention.

Light sources themselves may contribute to signal variation. FIG. 5 shows plot 500 of shot-to-shot signal variation of a xenon lamp plotted versus wavelength. For the data shown, solid curve 510, the minimum variation is approximately 0.5% but may be as large at 1.5% for certain wavelengths less than 350 nm. The data shown presents two concerns with flashlamp stability: firstly, shot-to-shot variation which changes the overall signal level and secondly, wavelength-dependant shot-to-shot variation. Shot-to-shot variation may be caused by arc motion or inconsistent arc formation. Although a source of measurement variation; overall, non-wavelength-dependant signal level variation may be addressed, in certain cases, with appropriate signal processing as this may be approximated with a uniform signal gain or offset value. However, wavelength-dependant shot-to-shot variation may not be easily addressed as it is not uniform shot-to-shot. Lamp aging that gradually changes the emission spectrum of the lamp is also a variable, which may contribute to measurement error.

Figure 6:
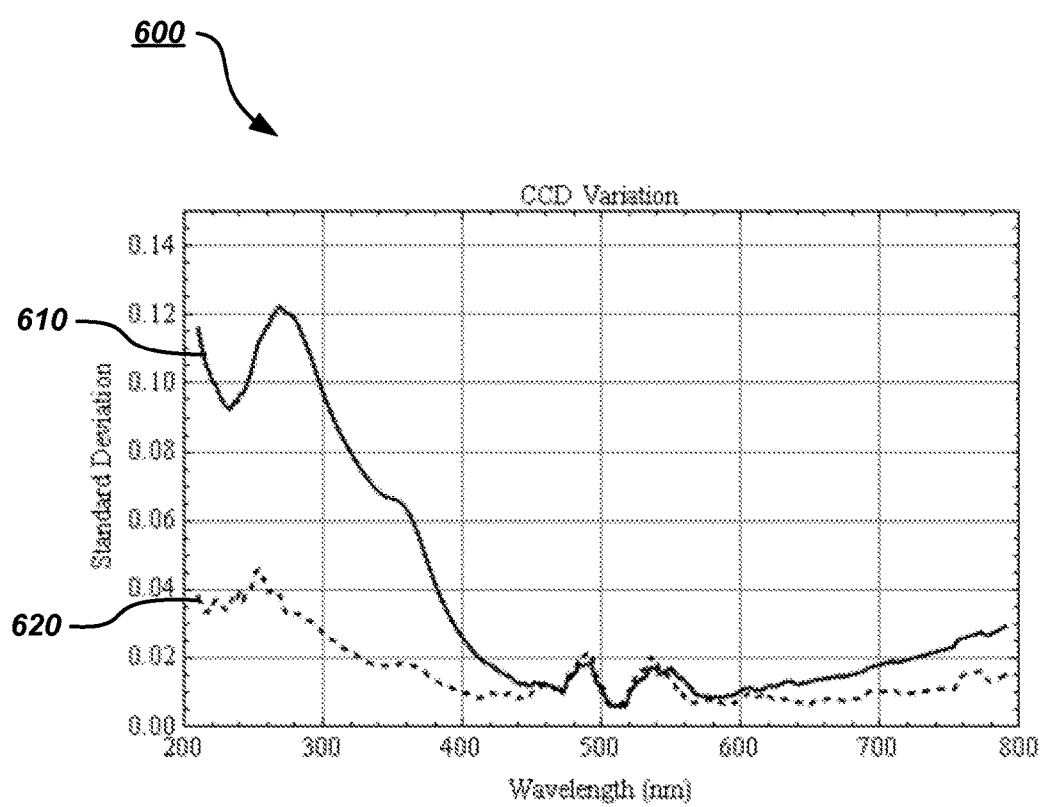
FIG. 6 is a plot of signal response variation within a CCD and between CCDs, in accordance with an exemplary embodiment of the present invention.

Elements of light analyzing devices may also contribute to signal variation and measurement error. FIG. 6 shows plot 600 of signal response variation within a representative CCD and between CCDs, which may be incorporated into a light analyzing device. The data shown is collected from areal imaging CCDs, such as S7031-series CCDs from Hamamatsu of Japan. Solid curve 610 shows the variation between multiple CCDs, and dashed curve 620 shows the variation within an individual CCD. Variation between CCDs may be 3× larger than for variation within individual CCDs. This increased variation makes the use of a 2-channel device, based upon an individual CCD, less prone to signal errors and variations than the use of multiple CCDs. Other elements, such as lens, gratings and filters, of light analyzing devices may also contribute to measurement error and variation.

From the foregoing it is apparent that optical measurements using prior art optical measurement systems are susceptible to signal errors and variations from many different sources. Some are predicable, linear and easily compensated while others are not. What is needed is an optical measurement system and operating method for mitigating these types of errors and variations and then for compensating for any remaining measurement error or variation. In accordance with various embodiments of the present invention, a novel optical measurement system is disclosed which enables the use of a novel signal error correction technique. Essentially, the presently described optical monitoring system is designed to eliminate as many sources of measurement error or variation as possible. However any remaining measurement error or variation is detected separately, using a reference signal, and that reference signal is used to compensate an associated measurement signal. More particularly, because the unmitigated measurement error or variation will always be present, even during optical calibrations, the reference signal is employed during the optical calibration phase. Still more particularly, light signal errors and variation generated by the system are addressed (using a dark measurement calibration), absolute or relative measurement accuracy is addressed (using a known reference standard measurement calibration) and measurement drift, variation and stability errors are addressed (using ratios of reference signals and measurement signals for the dark, known reference and production workpiece measurements).

Here it should be mentioned that the nomenclature used below can be somewhat confusing with regard to the term "references," employed hereinafter. The optical measurement system utilizes two, sometimes separate signal paths, a measurement light signal path (carrying a measurement light signal) and a reference light signal path (carrying a reference light signal). However, during the optical calibration of the optical monitoring system, a Dark calibration is performed, as well as a known Reference standard calibration. The known Reference standard calibration is different from, but utilizes the reference light signal received over the reference light signal path, as well as the measurement light signal. The distinction between the two, as well as other features and advantages of the present optical monitoring system will become apparent from the discussion of the separate embodiments below.

Figure 7:
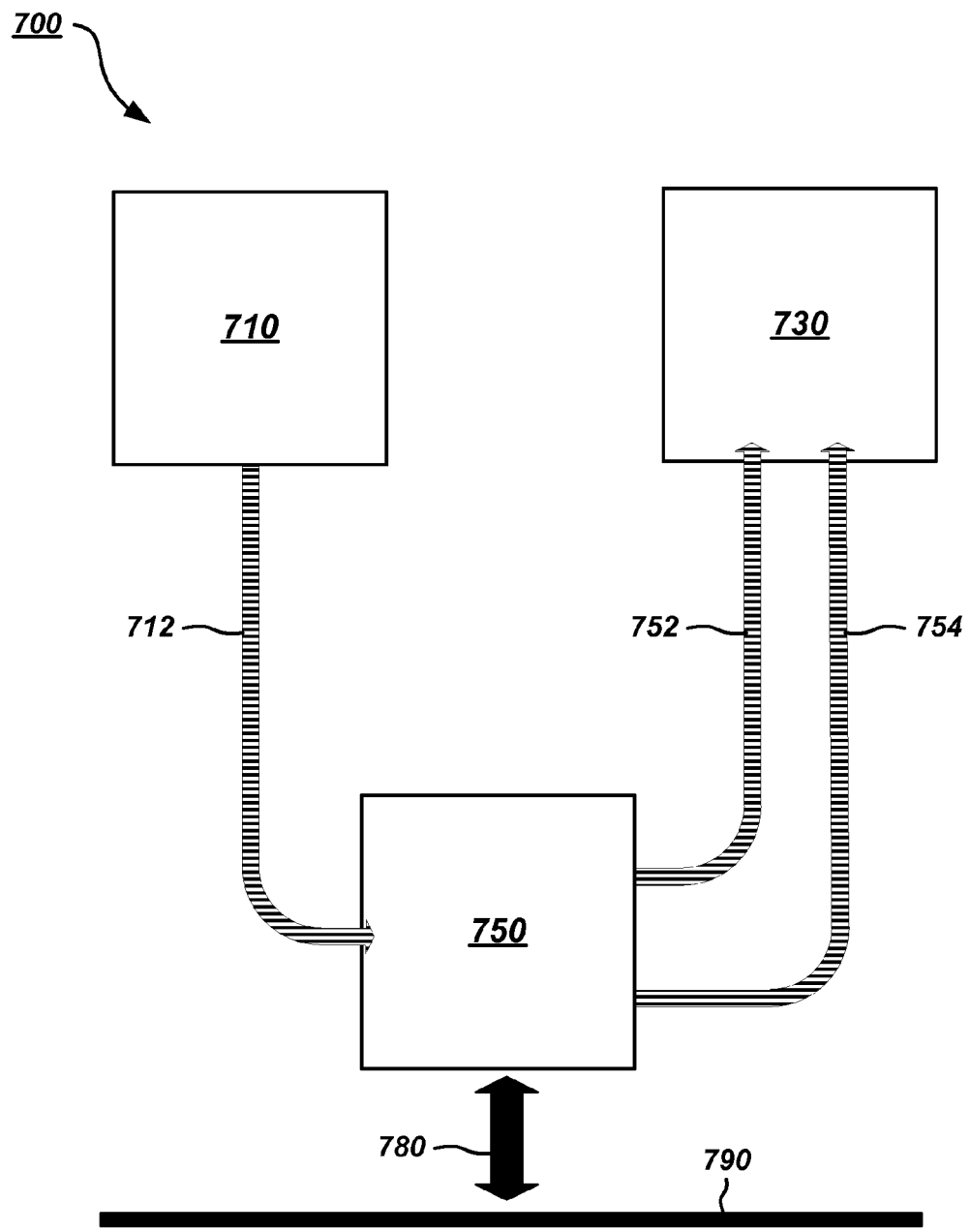
FIG. 7 is a pictorial schematic of an optical measurement system, in accordance with an exemplary embodiment of the present invention.

FIG. 7 shows a pictorial schematic of elements of optical measurement system 700 of the present invention arranged to reduce and/or compensate for the sources of drift, error and variability such as detailed herein above. Optical measurement system 700 includes flash illumination source 710, source optical fiber assembly 712, spectrograph 730, reference optical fiber assembly 752, measurement optical fiber assembly 754, optical assembly 750, workpiece interrogation light signal 780 and workpiece 790. Flash illumination source 710 is depicted connected via source optical fiber assembly 712 with optical assembly 750 to supply light signal 780 to workpiece 790. Spectrograph 730 is connected via reference optical fiber assembly 752 and measurement optical fiber assembly 754 with optical assembly 750 to receive both a reference light signal and a workpiece interrogation (measurement) light signal derived from light signal 780 after reflection from workpiece 790. Optical assembly 750 derives the reference light signal and the workpiece interrogation (measurement) light signal from a source light signal provided by flash illumination source 710.

Flash illumination source 710, for the purposes of the presently described invention, comprises a flash, strobe or flashlamp or other type of non-continuous illumination source. Alternatively flash illumination source 710 may also comprise a continuous illumination source that employs light shuttering, chopping or other means for generating a pulse of non-continuous light for the optical measurement system. The distinction between continuous and non-continuous light sources is important because as described herein below in association with FIG. 15, the optical measurement system may operate advantageously in the presence of background plasma light when the measurement light source is non-continuous.

Although advantageous for accommodating the presence of plasma light when operating, flash illumination source 710, may produce variations and measurement error from shot-to-shot instability, arc instability, oxygen/ozone absorption, solarization and lamp aging. Source optical fiber assembly 712, reference optical fiber assembly 752 and measurement optical fiber assembly 754 may produce variations in measurements due to short-term and long-term solarization. Spectrograph 730 may produce variations in measurements from oxygen/ozone absorption and CCD variation. Optical assembly 750 may produce variations in measurements due to oxygen/ozone absorption and sub-element solarization. Not all measurement variation producing sources are listed herein; other elements and sub-elements of optical measurement system 700 may also contribute to measurement variation and may be reduced and/or compensated by the arrangement of optical measurement system 700 as shown in FIG. 7.

Shot-to-shot instability, arc instability, oxygen/ozone absorption and lamp aging of flash illumination source 710 may be reduced and/or compensated by making these variations common to the reference and measurement signals, which when ratioed may remove or reduce these variations. In accordance with one exemplary embodiment of the present invention, these variations are made common by transmitting the source light from flash illumination source 710 via source optical fiber assembly 712 to optical assembly 750 which uses an optical sub-element to partition the source light into the correlated reference and measurement light signals. The short-term and long-term solarization variations arising from source optical fiber assembly 712 may be addressed in the same manner as it is common to both the reference and measurement light signals.

In order to ensure that the ratioing methodology disclosed below with regard to EQNS. 1-11 functions as described, the light path of the reference signal should be as optically equivalent as possible to the light path for the measurement signal. Optimally, the optical elements in the measurement light path should be common to the optical elements in the reference light path, thereby assuring that the magnitude and signature of any signal variations arising from these elements will be common to both light paths. Absolute commonality is generally not possible for the optical elements following the partitioning of the source light because the reference and measurement light paths are different. Specifically, the measurement light path includes the workpiece but the reference light path does not. Therefore, to preserve commonality of the signal variations as much as possible, all optical elements in the reference light path are optically matched to the optical elements in the measurement light path. That is to say, the light paths are optically matched so that signal errors, drift and variations produced in the reference light path are common (equivalent or are at least proportional) to the signal errors, drift and variations produced in the measurement light path. It should be understood that the light paths include not only the optical light paths but also includes other signal paths, based upon transformed light signals, such as electronic and data paths within a light analyzing device.

Solarization is a particular problem inherent in many silica optical components, and attenuation may increase proportionally with the length of the optical path through the silica, hence, optical fibers are particularly susceptible to solarization effects (see FIG. 4 above). These signal variations cannot be eliminated, especially if fiber optic cable is used in the system. Therefore, the measurement light signal should be compensated for these variations. Essentially, this is achieved by detecting and quantifying the signal variation, for instance, by use of a light path that is unaffected by the workpiece measurement being made, i.e., the reference light path. As mentioned above, the reference signal is only useful if 1) the amount of variation can be quantified from the reference signal; and 2) the magnitude of variation on the reference signal is equivalent to or at least proportional to the magnitude of variation on the measurement signal.

The short-term and long-term solarization variations arising from reference optical fiber assembly 752 and measurement optical fiber assembly 754 may be addressed by matching the type, length, fiber count and overall optical signal levels of the two assemblies. Additionally, low-solarization optical fiber such as FDP/FDA-series fiber from Polymicro Technologies of Phoenix, Ariz.; or Optran UVNS-series fiber from Ceramoptec of East Longmeadow, Mass. may be used for the fabrication of any of the aforementioned optical fiber assemblies. The setting of optical signal levels of reference optical fiber assembly 752 and measurement optical fiber assembly 754 is discussed herein below in association with FIG. 12.

The oxygen/ozone absorption and CCD variation effects may be addressed in spectrograph 730 by utilizing a multi-channel, imaging spectrograph with, an areal imaging CCD. An imaging spectrograph separately images different regions of the slit onto distinct regions of the detector in the focal plane. The slit, optics, grating and other sub-elements are therefore common to the measurements of the separate channels. An example of an areal imaging CCD is the S7031-series by Hamamatsu Photonics of Hamamatsu City, Japan. An example of a multichannel imaging spectrograph is SD1024 spectrograph by Verity Instruments of Carrollton, Tex. This arrangement, as indicated by the CCD variation data of plot 600 illustrated in FIG. 6, may reduce variation in the important wavelength region below 300 nm on the order of 3×.

The oxygen/ozone absorption and sub-element solarization effects in optical assembly 750 may be addressed by common path purging, matched low-solarization optics, reflective optical elements and the utilization of an uncoated low-solarization silica plate beamsplitter. Details of embodiments of optical assembly 750 are discussed herein below in association with FIGS. 10A-E and 11A-B.

As may be appreciated from the foregoing, because of the matching and commonality of the reference light path to the measurement light path of the present optical measurement system, the intensity of the two light signals should be proportional, with the exception of changes in the measurement light signal due to interrogation of workpiece 790, via light signal 780. Any signal variation detected in a calibrated reference light signal will be due to absorption, solarization, lamp variation or other effects. Since an equivalent or at least proportional signal variation will present in a calibrated measurement light signal, the reference light signal can be used to correct the measurement light signal.

Figure 8A:
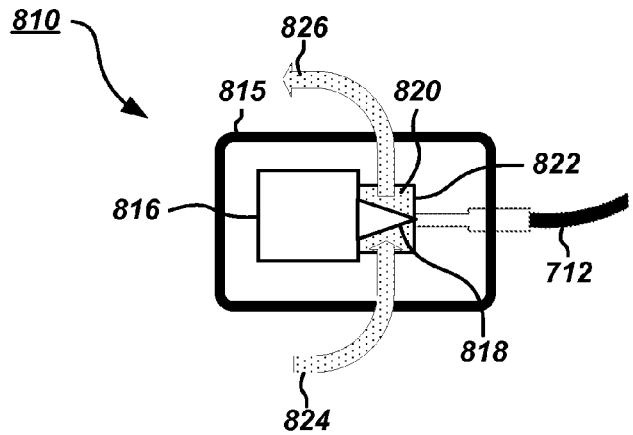
FIGS. 8A, 8B and 8C are pictorial schematics of portions of the optical measurement system of FIG. 7 showing further details, in accordance with an exemplary embodiment of the present invention.
Figure 8B:
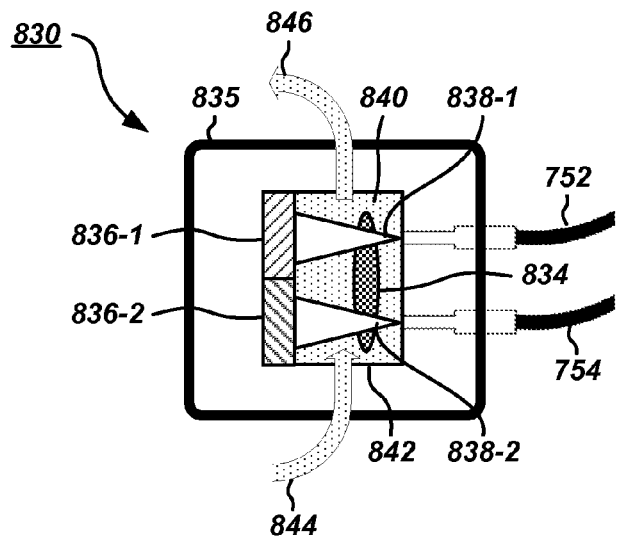
Figure 8C:
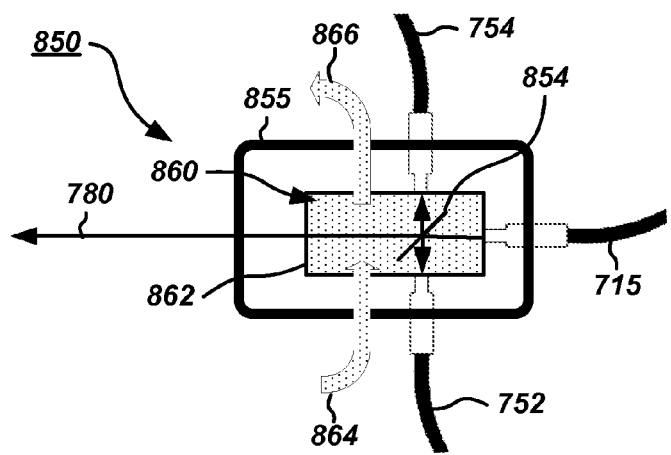

FIGS. 8A, 8B and 8C are pictorial schematics of portions 810, 830 and 850 of the optical measurement system of FIG. 7 showing further details and features in accordance with various exemplary embodiments of the present invention. Flash assembly 810 of FIG. 8A shows internal elements of flash illumination source 710. Spectrograph assembly 830 of FIG. 8B shows internal elements of spectrograph 730. Optical assembly 850 of FIG. 8C shows internal elements of optical assembly 750. FIGS. 8A, 8B and 8C are described in light of the generic optical system illustrated in FIG. 7, wherein corresponding assembly elements and sub-elements are designated using corresponding element numbers. Here it should be mentioned that this notation is intended merely to simplify the description of the present invention and is not meant to limit the scope of the present invention solely to that shown in FIG. 7. Artisans of ordinary skill in the relevant art would readily understand that the advantages of the present invention as described herein would be readily applicable to other embodiments that are not specifically disclosed. Using the discussions herein of how to make and use the presently described invention, ordinarily skilled artisans would easily apply these teachings to those non-disclosed, but obvious embodiments without departing from the scope and spirit of the presently described invention.

Enclosed within flash assembly housing 815 of flash assembly 810 for flash illumination source 710 are purged volume 820 and lamp 816. Purge gas, for instance an inert gas such as nitrogen, is contained in sealed flash assembly containment housing 822 that encapsulates as much as practical or required of the path of source light signal 818, in order to reduce or eliminate errors in the light signals resulting from absorption by ozone and/or oxygen in the optical signal path from UV and DUV radiation exposure generated by source signal light 818 itself. Although not necessary, flash assembly containment housing 822 may also be constructed such that all or portions of lamp 816 and an optical terminator for source optical fiber assembly 712 are contained therein. The purge gas is directed into purged volume 820 via inlet 824 and directed out of purged volume 820 via exhaust 826. One advantage of utilizing a purged volume over prior art flash assemblies without a purged volume is that by purging purged volume 820, all oxygen and ozone can be removed from the area surrounding source light signal 818, between lamp 816 and optical fiber assembly 712, that may absorb source light signal 818.

For the purposes of describing the present invention, optical fiber assembly 712 is considered optional as there may be embodiments wherein flash assembly 810 (or a flashlamp integrated therein) is optically coupled directly to optical assembly 850, without an intervening optical fiber assembly. Recall also that flash illumination source 710 is a non-continuous illumination source that may comprise a flash, strobe or flashlamp or other type of non-continuous illumination source, or alternatively comprise a continuous illumination source that employs a light shuttering mechanism. The same distinction exists for flash assembly 810.

The arrangement of internal elements of flash illumination source 710 provides that the lamp, purging and light paths are each common to both the reference light path and the measurement light path in order to reduce and/or compensate for variation and measurement error, for the reasons discussed above. Here, source light signal 818 is the common light source for both measurement light (for instance carried by signal optical fiber assembly 754) and reference light (for instance carried by reference optical fiber assembly 752). Each will be described below in greater detail. This commonality assures that any variation, drift or measurement error will be common (equivalent or at least proportional) to both light paths, which is necessary for utilizing a ratio of averages of the signals discussed below with regard to EQNS. 1-10 for calibrating, compensating and stabilizing the measurements. Hence, while it is technically possible to generate reference light from one light source and measurement light from a second light source, commonality would be destroyed as it would not be possible to accurately assess variation, drift or error in one light source using reference measurements taken from the other (see the discussion of the processes depicted in FIGS. 12 and 13 and, again, EQNS. 1-10 below). As an aside, this principle is demonstrated in FIG. 6 above, with regard to using multiple CCDs.

Turning now to FIG. 8B, enclosed within spectrograph assembly housing 835 of spectrograph assembly 830 of spectrograph 730 are purged volume 840, purged volume containment housing 842, optics 834 and an image sensor, for example a CCD type device depicted as CCD detector 836, which is further comprised of first (reference) CCD channel 836-1 and second (measurement) CCD channel 836-2, discussed further below. Here again, a purge gas such as nitrogen may be directed into purged volume 840 via inlet 844 and directed out of purged volume 840 via exhaust 846. As is well understood in the relevant art, light signals received at spectrograph assembly 830 are projected through spectrograph optics 834 and onto CCD 836 to be proportionally converted from optical intensity signals to electrical signals, usually over a plurality of wavelengths. Similarly, as discussed above with regard to flash assembly 810, purging purged volume 840 removes oxygen and ozone from the light path that may see portions of light signal 838 emitted from the optical fiber assemblies.

A pair of light signals is received at spectrograph assembly 830 from optical assembly 850, illustrated as reference light signal 838-1, from reference optical fiber assembly 752 and measurement light signal 838-2, from measurement optical fiber assembly 754. In an effort to preserve commonality, common CCD detector 836 is employed for converting both the reference light signal and the measurement light signal, by subdividing CCD detector 836 into two matching CCD channels, first CCD channel 836-1 for converting the reference light signal and second CCD channel 836-2 for converting the measurement light signal. Reference light signal 838-1 and measurement light signal 838-2 pass through common purged volume 840 for a common distance, through common spectrograph optics 834 (focusing optics, collimating optics, slits, etc.) onto matching channels of common CCD 836 (reference CCD detector channel 836-1 and measurement CCD detector channel 836-2). As mentioned above, this commonality enables the reduction and/or compensation of variation, drift and measurement error associated with the light signal(s).

With further regard to reference and measurement optical fiber assemblies 752 and 754, although it is not possible to use a common fiber for both the measurement and reference signals, it is possible to match the fiber assemblies with such precision that commonality is essentially preserved. Hence, reference and measurement optical fiber assemblies 752 and 754 are essentially identical (matching) optical assemblies, having matching composition types, lengths, fiber counts, terminating optics, optical properties, etc., for achieving comparable optical signal levels of the two assemblies. Moreover, matching the optical fiber assemblies will ensure that any drift or variation of the light signal on one optical fiber assembly due to a degradation of the optical fiber assembly, the optical terminator, etc., would be common to the light signal of the opposite optical fiber assembly. Consequently, by employing matching optical fiber assemblies, any changes detected in the reference light signal can be quantified and used for correcting the measurement light signal. Here again, for the purposes of describing the present invention, reference optical fiber assembly 752 and measurement optical fiber assembly 754 are considered optional because it is possible to optically couple spectrograph assembly 830 directly to optical assembly 850, without intervening optical fiber assemblies.

With regard to the internal components of optical assembly 750, illustrated in FIG. 8C as optical assembly 850, initially it should be noted that optical assembly 750 provides the illumination and collimation/focusing optics for generating workpiece interrogation light signal 780 for interrogating workpiece 790. The path of interrogation light signal 780 is part of the measurement light path and not part of the reference light path. Consequently, aside from providing workpiece interrogation light signal 780, optical assembly 850 also partitions the source light signal into a reference light signal and an interrogation light signal 780, which is collimated as the measurement light signal. Therefore, while optical assembly 850 may contain some optical components common to both the reference and measurement light signal paths, optimally, the components in only the reference light path should optically match those in the measurement light path.

Enclosed within housing 855 of optical assembly portion 850 of optical assembly 750 are purged volume 860, purged volume containment housing 862, and optics 854 (represented simply as a beamsplitter). Purge gas, such as nitrogen, may be directed into purged volume 860 via inlet 864 and directed out of purged volume 860 via exhaust 866. Purging purged volume 860 removes oxygen and ozone that may absorb light signals emitted from source optical fiber assembly 712 and received by reference optical fiber assembly 752 and/or signal fiber assembly 754 in the manner discussed above. In association with FIG. 8C and FIGS. 10A-E and 11A-D, notice that light signals from reference optical fiber assembly 752 and measurement optical fiber assembly 754 pass through certain common components within optical assembly 850, e.g., beam splitter, purged volumes, etc., although other components within optical assembly 850, e.g., focusing and collimating optics, are in only the path of the measurement signal. Optimally, the reference light signal and measurement light signal may pass through common purged volume 860 for a common distance. Prior to beam splitting within optical assembly 850 and interrogation, the source light signal from source optical fiber assembly 712 need not pass through common optical components (or a matching distance) because the source light signal essentially comprises both a measurement light signal and a reference light signal. Hence, any signal variations that occur in the source light signal is detectable on the reference light signal.

Figure 9:
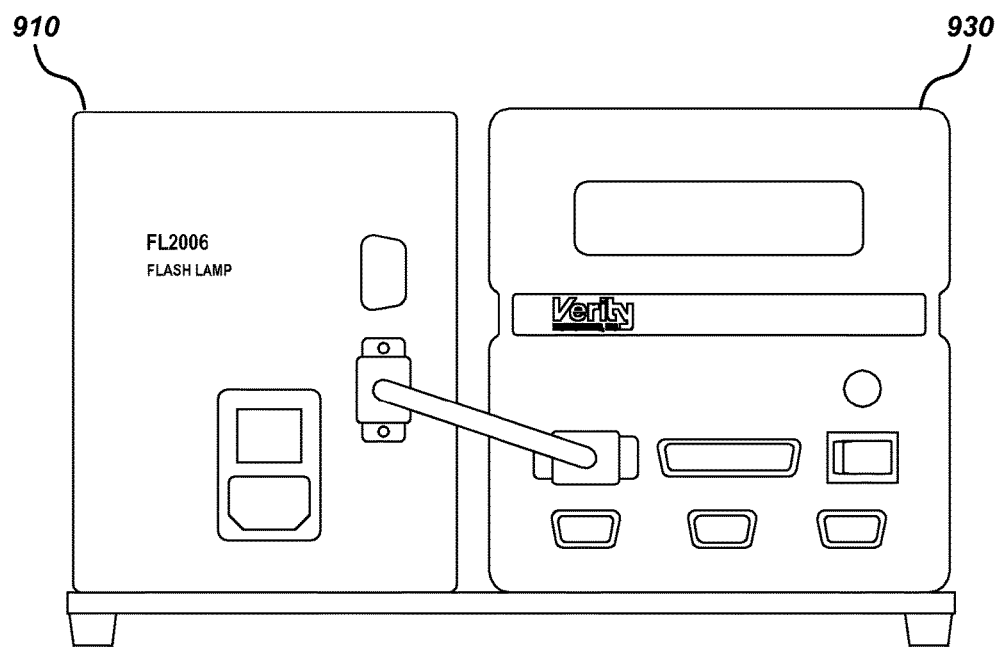
FIG. 9 is a front view of a spectrograph and flashlamp configurable for use with the optical measurement system of FIG. 7, in accordance with an exemplary embodiment of the present invention.

FIG. 9 shows a front view of spectrograph 930 and flashlamp 910 configured for use with the optical measurement system of FIG. 7 in accordance with one exemplary embodiment of the present invention. In addition to elements for timing control, data conversion and communications with external systems, spectrograph 930 includes elements described in FIG. 8A to control variation due to CCD variation as well as oxygen and ozone absorption. In addition to elements for lamp intensity control and triggering; flashlamp 910 includes elements described in FIG. 8B to control signal variation due to lamp variation, as well as oxygen and ozone absorption.

Figure 10A:
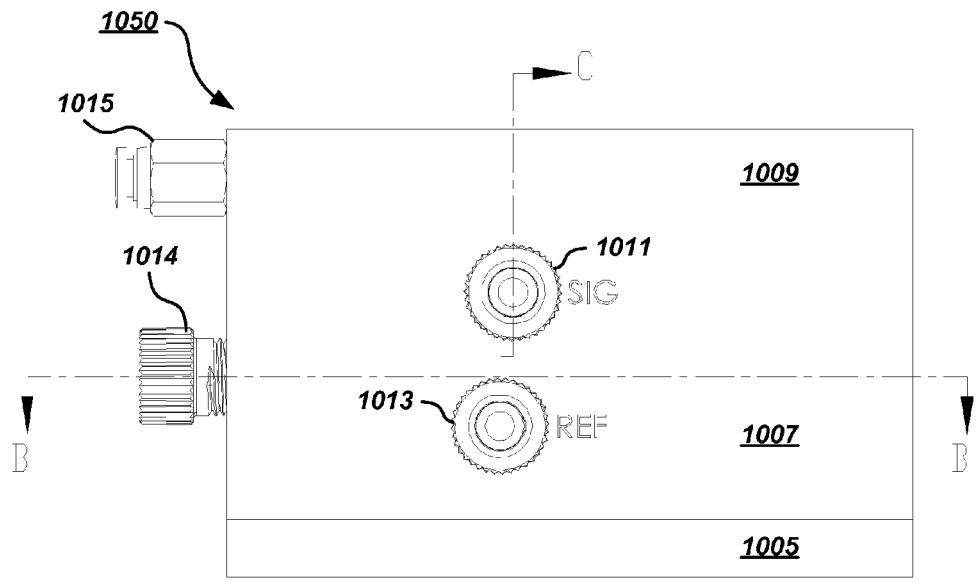
FIGS. 10A and 10B are a side-view and top-view, respectively, of an optical assembly configurable for use with the optical measurement system of FIG. 7, in accordance with an exemplary embodiment of the present invention.
Figure 10B:
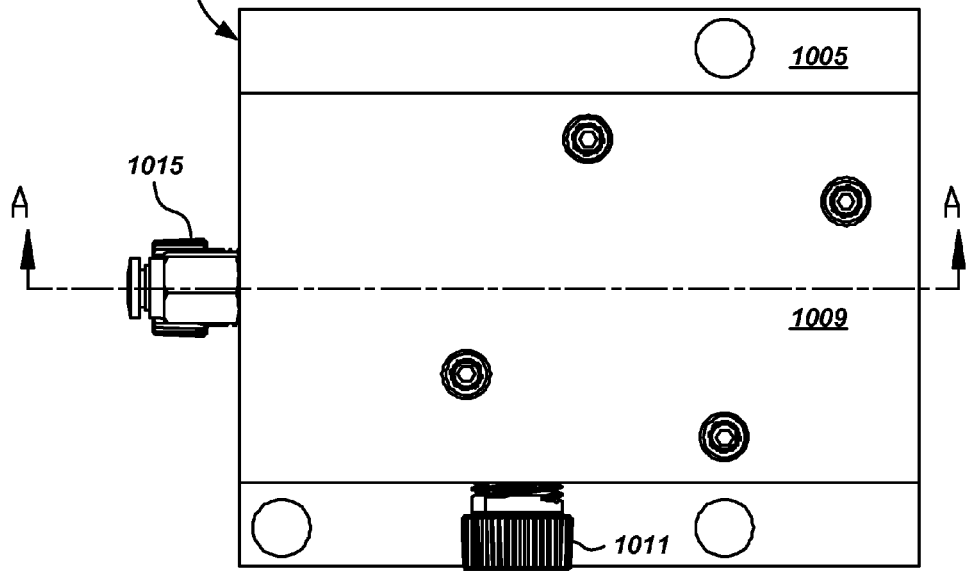

FIGS. 10A and 10B show a side and top view, respectively, of optical assembly 1050 configured for use with the optical measurement system of FIG. 7 in accordance with an exemplary embodiment of the present invention. Although described herein below as designed for collimation of light signals directed toward a workpiece; optical assembly 1050 may, in other exemplary embodiments by exchange of sub-elements, be configured for focusing light directed toward a workpiece or other optical function. Optical assembly 1050 includes a multipart body including base plate 1005, main body 1007 and top plate 1009. Other body configurations of body parts are also possible. Main body 1007 includes fiber retention fittings 1011, 1013 and 1014 used to retain a measurement optical fiber assembly (e.g., element 754 of FIGS. 7, 8B and 8C), a reference optical fiber assembly (e.g., element 752 of FIG. 7) and a source optical fiber assembly (e.g., element 712 of FIGS. 7, 8A, 8B and 8C). Top plate 1009 includes gas fitting 1015 for permitting entry of a purge gas into optical assembly 1050. Although not shown, optical assembly may include an additional port or gas fitting permitting exit of a purge gas.

Figure 10C:
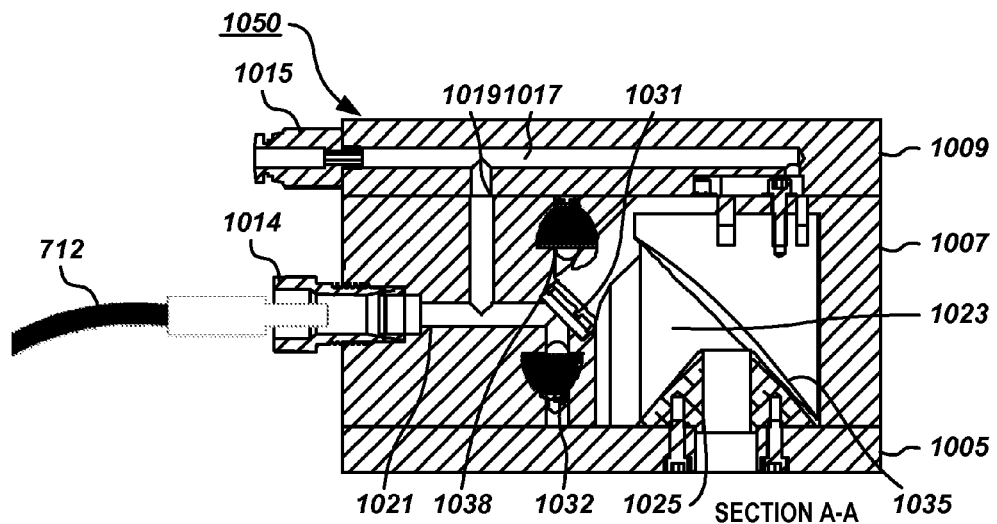
FIGS. 10C, 10D and 10E are cross-sectional views of the optical assembly of FIGS. 10A and 10B along section lines A-A, B-B and C-C, respectively, showing interior details of the optical assembly of FIGS. 10A and 10B, in accordance with an exemplary embodiment of the present invention.
Figure 10D:
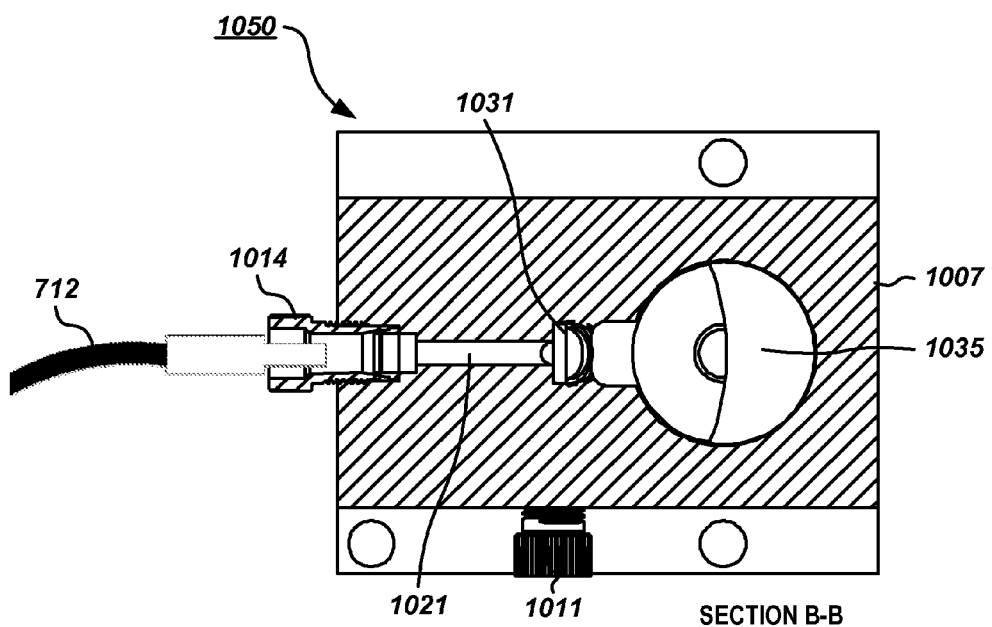
Figure 10E:
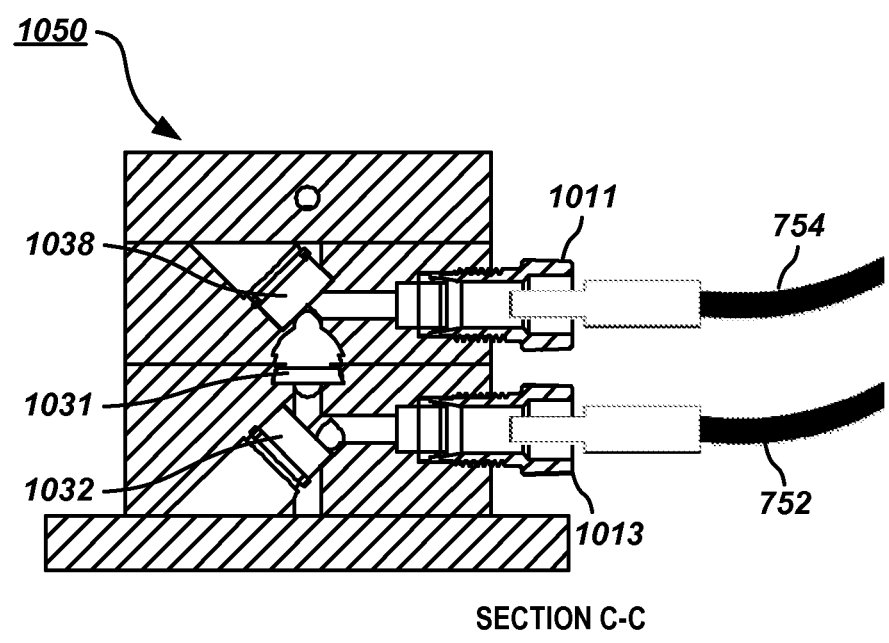

FIGS. 10C, 10D and 10E show cross-sectional views of optical assembly 1050 of FIGS. 10A and 10B along section lines A-A, B-B and C-C, respectively, showing interior details of optical assembly 1050. As shown, gas fitting 1015 is connected with purge passages 1017, 1019 and 1021, which permit purging of light paths of oxygen and ozone. Purge gas entering via gas fitting 1015 ultimately passes through cavity 1023 and exits optical assembly 1050 via an opening in light cone 1025. Source optical fiber assembly 712 may be inserted into and retained by retention fitting 1014. Light exiting from source optical fiber assembly 712, travels along purge passage 1021 and is reflected from beamsplitter 1031 toward mirror 1032. Subsequent to reflection from mirror 1032, light may be incident upon reference optical fiber assembly 752 for transmission to a spectrograph as shown in FIGS. 7, 8B and 8C. As well as reflecting from beamsplitter 1031, some portion of the light is transmitted toward off-axis parabolic mirror 1035 which collimates the incident light forming a collimated beam, which is directed through an opening in light cone 1025 toward a workpiece (not shown). Upon reflection from the workpiece, light is incident upon off-axis parabolic mirror 1035 which now focuses the light toward beamsplitter 1031 and mirror 1038. Subsequent to reflection from beamsplitter 1031 and then mirror 1038, light may be incident upon measurement optical fiber assembly 754 for transmission to a spectrograph as shown in FIGS. 7, 8B and 8C.

Figure 11A:
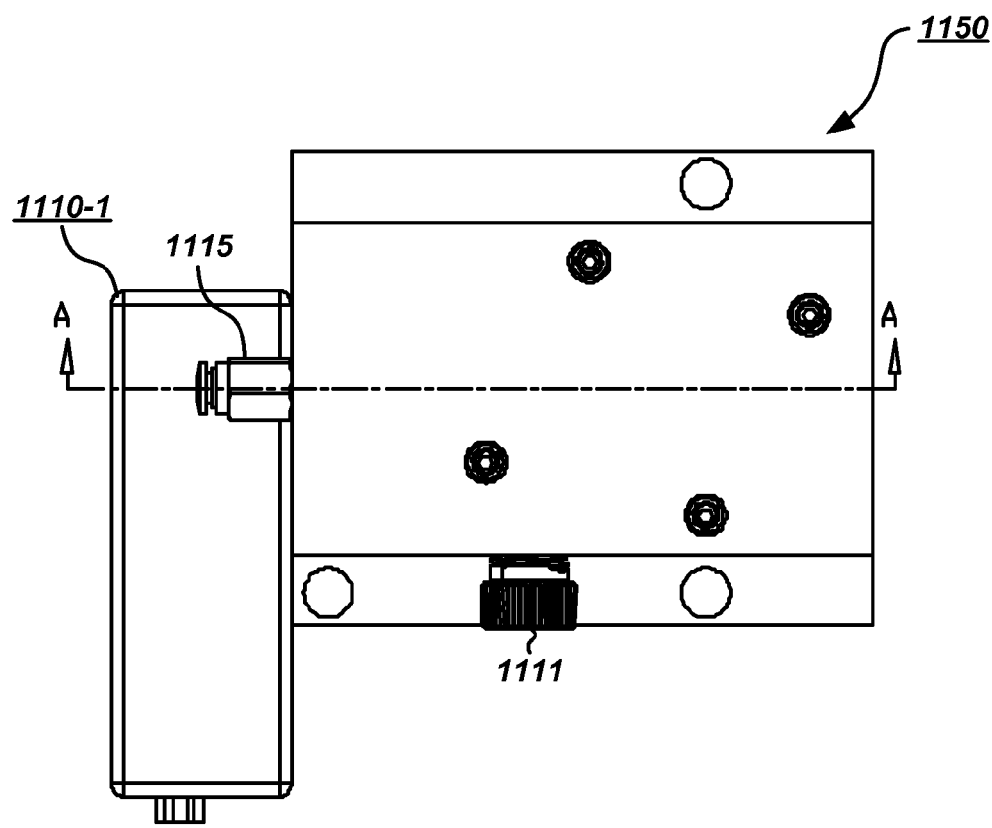
FIGS. 11A and 11B are a top-view and cross-sectional view, respectively, of alternate constructions of an optical assembly with an integrated miniature light source configurable for use with an optical measurement system, in accordance with an exemplary embodiment of the present invention.
Figure 11B:
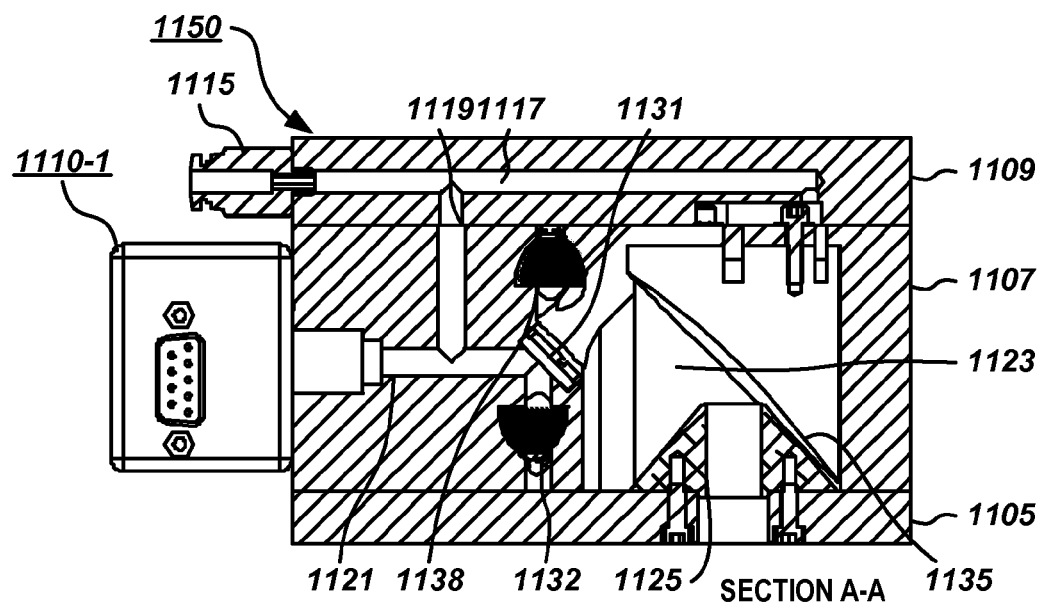

FIGS. 11A and 11B show a top view and cross-sectional view, respectively, of alternate constructions of an optical assembly with integrated miniature light source configurable for use with an optical measurement system in accordance with another exemplary embodiment of the present invention: FIGS. 11A and 11B show a construction wherein a miniature flash assembly 1110-1 is integrated with optical assembly 1150 and therefore eliminates the use of a source optical fiber assembly such as source optical assembly 712 (not shown) of FIGS. 7, 8A, 8B and 8C. Flash assembly 1110-1 may be a compact flashlamp product such as the model 9456 available from Hamamatsu of Hamamatsu City, Japan.

Figure 11C:
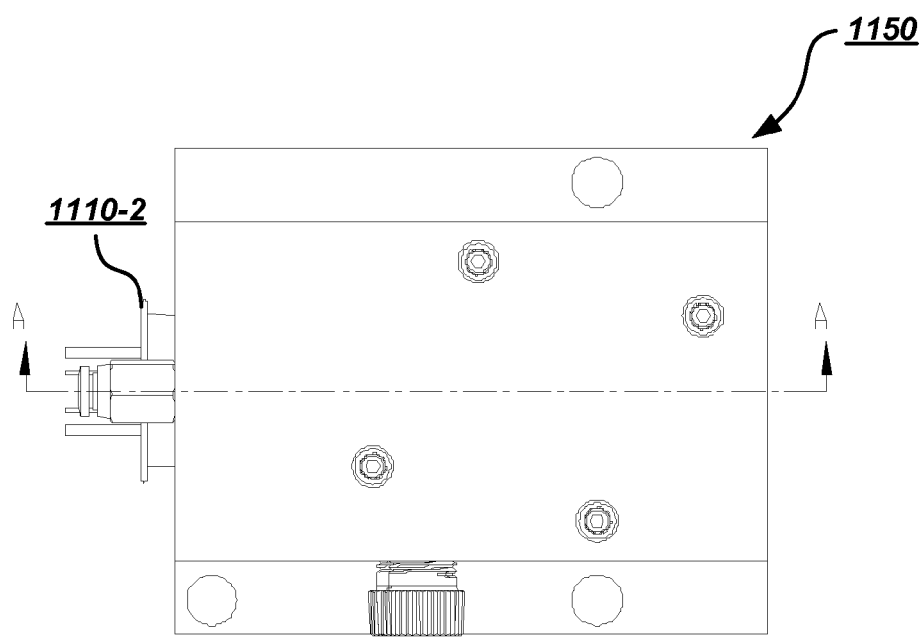
FIGS. 11C and 11D are a top view and cross-sectional view, respectively, of alternate constructions of an optical assembly with an integrated lamp configurable for use with an optical measurement system, in accordance with an exemplary embodiment of the present invention.
Figure 11D:
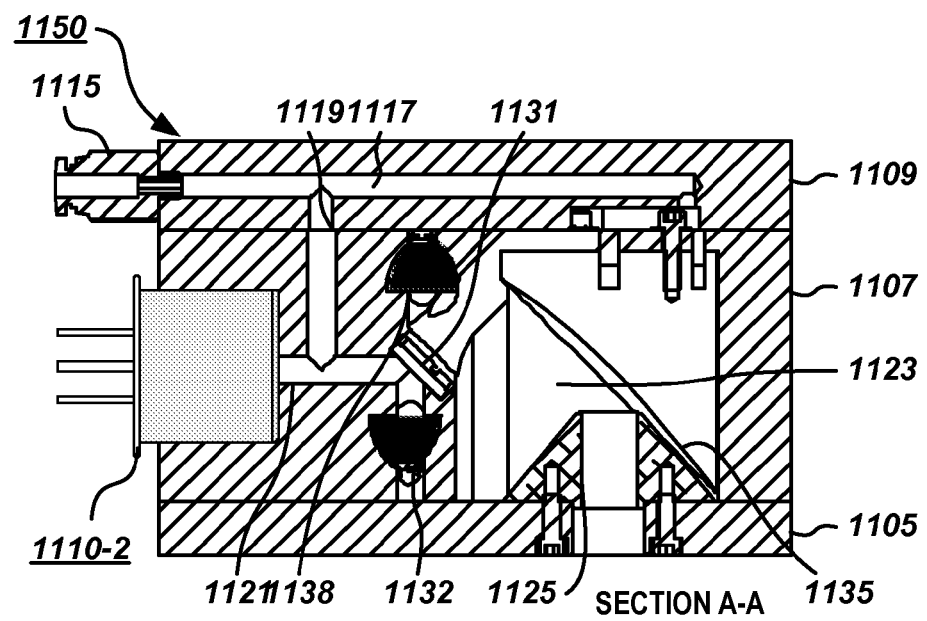

FIGS. 11C and 11D show a top view and cross-sectional view, respectively, of alternate constructions of an optical assembly with an integrated lamp configurable for use with an optical measurement system. FIGS. 11C and 11D show a construction wherein a flashlamp bulb 1110-2 is integrated with optical assembly 1150 and, therefore, eliminates the use of a source optical fiber assembly such as source optical assembly 712 of FIG. 7. Flashlamp bulb 1110-2 may be a bulb such as an FX1161 series bulb available from Excelitas Technologies of Waltham, Mass. The use of alternate constructions of the optical assembly permits variation in lamp size and power as well as allows physical constraints such as size, weight and/or thermal issues to be accommodated.

Figure 12:
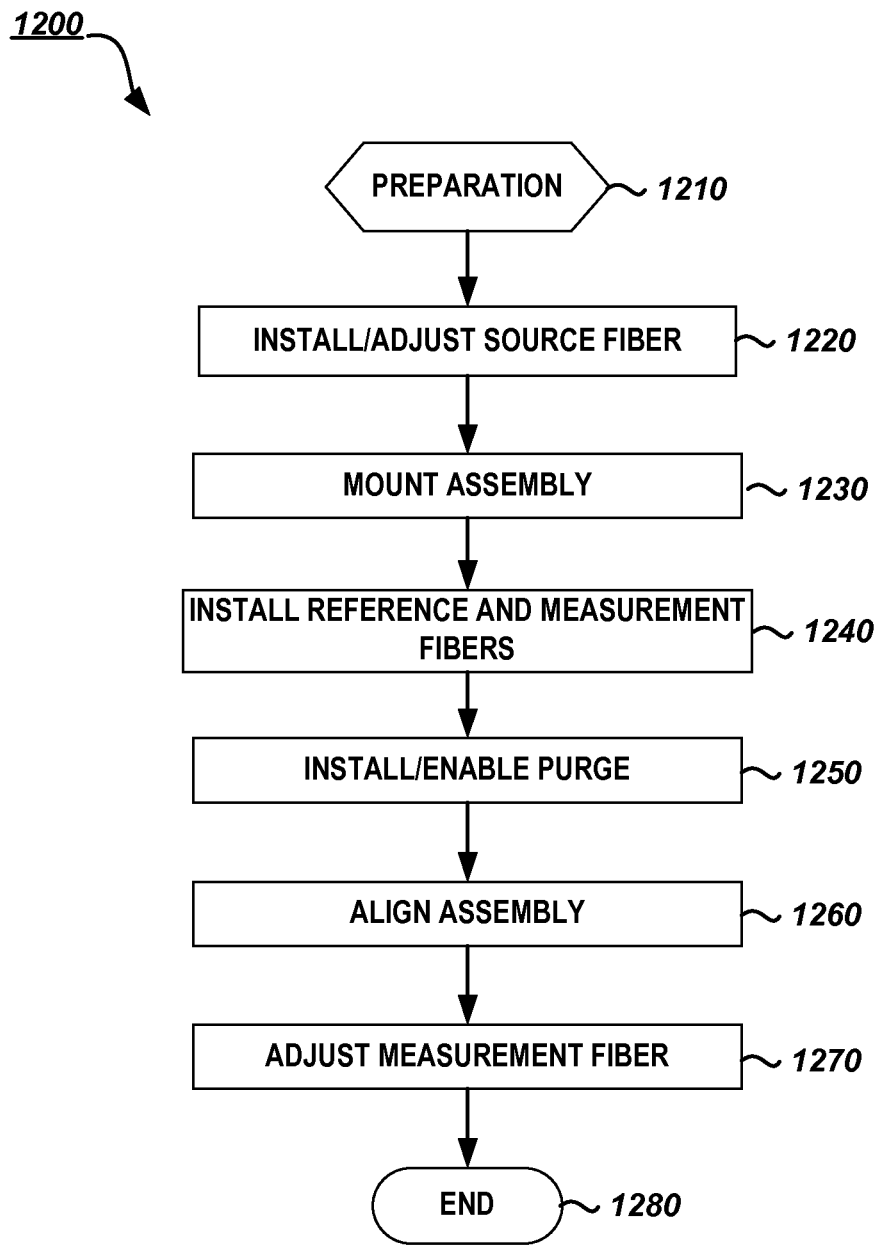
FIG. 12 is a flow chart of a process for installing and configuring an optical measurement system, in accordance with an exemplary embodiment of the present invention.

FIG. 12 shows a flow chart of process 1200 for installing and configuring an optical measurement system. Process 1200 begins with preparation step 1210 wherein any necessary or desired setup, configuration, supply and/or transport of a measurement system are performed. Additionally, or optionally, power to a measurement system may be supplied during step 1210, such as by activating a power switch or supplying external power. Process 1200, next advances to step 1220 wherein a source optical fiber assembly of a measurement system is installed and adjusted within an optical assembly. For an optical assembly with an integrated flashlamp, such as shown in FIGS. 11A and/or 11B, step 1220, may not be performed. The adjustment of the source optical fiber assembly may be performed to determine the focal point of the optical system so that the light exiting the source optical fiber assembly may be collimated or focused by a subsequent optical element, such as off-axis parabolic mirror 1035 of FIGS. 10A-E.

Next, in step 1230 the optical assembly may be mounted to a machine wherein workpieces are acted upon and will be monitored by the measurement system. Next in step 1240, reference and measurement optical fiber assemblies may be installed to an optical assembly by loosening and tightening of retention fittings such as retention fittings 1011 and 1013 of FIGS. 10A-E. In step 1250, purging system elements may be installed and purge gas may be supplied to a purge gas inlet to purge the optical assembly of oxygen and/or ozone. Following purging during step 1250, alignment of the optical assembly may be performed during step 1260. Alignment of the optical assembly may be performed to optimize signal intensity and/or to set perpendicularity of the collimated light to the workpiece surface. Next in step 1270, adjustment of measurement optical fiber assembly may be performed to provide equalization of the reference and signal intensities whereby minimizing differential solarization between signal and reference optical fiber assemblies. Upon satisfactory performing the abovementioned steps, process 1200 terminates with step 1280. At the termination of step 1280 the measurement system is prepared for operation and measurement of workpieces.

Figure 13:
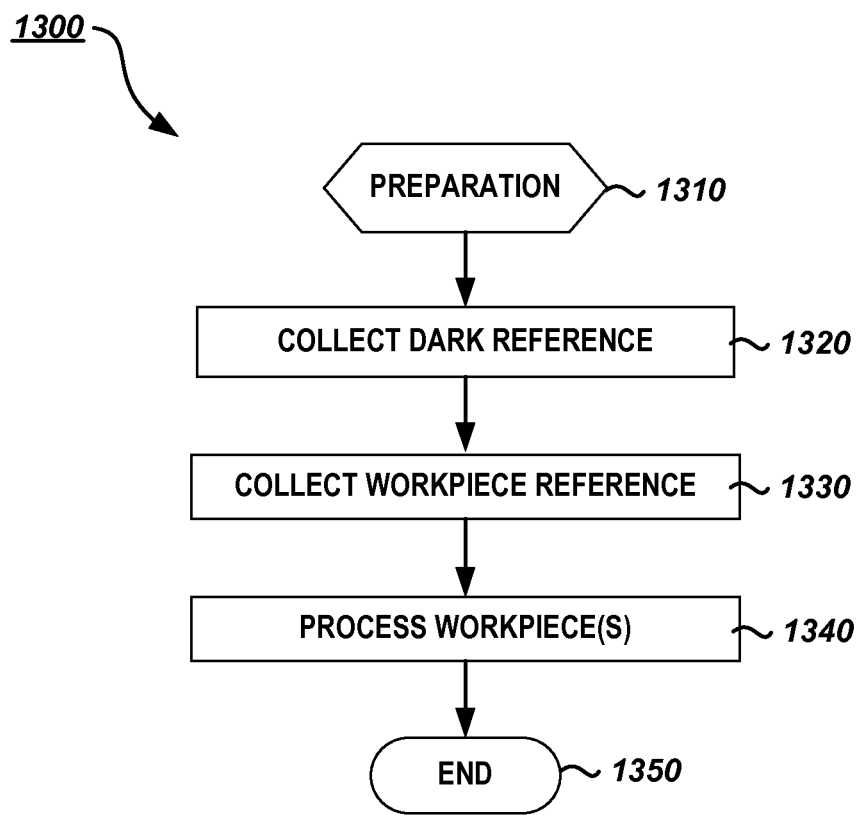
FIG. 13 is a flow chart of a process for operating an optical measurement system, in accordance with an exemplary embodiment of the present invention.

FIG. 13 shows a flow chart of process 1300 for operating an optical measurement system in accordance with an exemplary embodiment of the present invention. Process 1300 begins with preparation step 1310 wherein any necessary or desired setup or configuration of a measurement system is performed. Additionally, or optionally, reference materials as required herein below may be prepared during step 1310. Process 1300, next advances to step 1320 wherein a dark reference signal is collected/processed and stored for the reference and measurement signals. For collection of a dark reference signal, a workpiece of low reflectivity or other element is placed in the location of the workpiece to be measured so as to either absorb any incident light or direct any incident light away so as to not return to the measurement system. For example, a tilted mirror or specularly reflective workpiece such as a silicon wafer may be used. This procedure permits isolation of any light signals derived from the elements of the measurement system or processing equipment.

Next in step 1330, a known workpiece reference signal is collected/processed/stored for future use from the reference and measurement signals. For collection of a workpiece reference signal, a workpiece of known optical properties is placed in the location of the workpiece to be measured so as to reflect incident light back toward the measurement system as would a workpiece undergoing measurement. For example, a specularly reflective workpiece such as a silicon wafer may be used and electrostatically chucked into a workpiece operating position. This procedure permits determination of light signals derived from the workpiece.

When combined with the dark reference signal, the workpiece reference signal permits isolation of light signals exclusively from the workpiece undergoing measurement. Upon satisfactory performing the abovementioned steps, process 1300 advances to step 1340 wherein processing of one or more workpieces is performed using data derived from the collection of the light signals of steps 1320 and 1330. After any workpieces have been processed, process 1300 terminates with step 1350.

Figure 14:
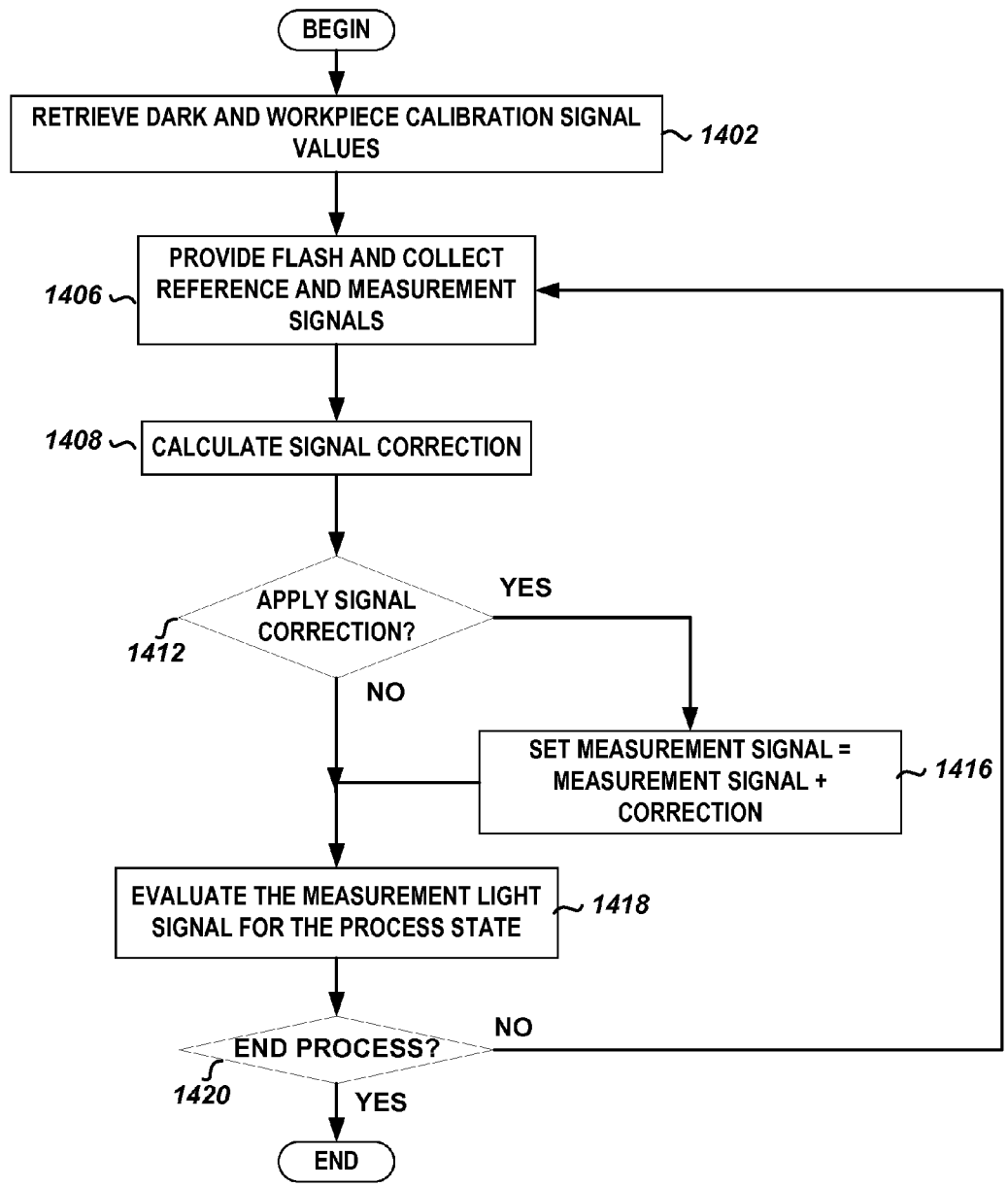
FIG. 14 is a flow chart which depicts a method for processing workpieces using measurement signals corrected for variations and errors due to absorption and solarization effect in accordance with an exemplary embodiment of the present invention.

FIG. 14 is a flow chart which depicts a process for processing workpieces using measurement signals corrected for variations and errors due to absorption, solarization and other affects in accordance with an exemplary embodiment of the present invention. The process depicted in FIG. 14 is represented by process step 1340 in FIG. 13 above. The method begins by retrieving the previously collected/processed dark calibration values (<Dark>) and the Reference calibration values (<Reference>) that will be necessary for compensating signal variation, as well as for evaluating the state of the production process (step 1402). These are ratioed values of reference light signal values and measurement light signal values collected for respective dark and known reference samples that were collected in steps 1320 and 1330 discussed above with regard to the previous flow chart and discussed below with regard to EQNS. 1-11 below.

Next, with a workpiece in place for interrogation, a flash is provided by flash illumination source 710, and the reference light signal and measurement light signal are collected at spectrograph 730 (step 1406). At least one ratio of a monitored reference light signal and monitored measurement light signal is necessary for compensating signal variation in the measurement signal derived from the current workpiece. In step 1408, the current monitored reference light signal and the current monitored measurement light signal are mathematically combined with the dark and reference calibration values to calculate the measurement signal correction. This calculation step may be omitted in subsequent passes on the same wafer, performed intermittently for various samples of the same wafer, or even performed only once and used for several production wafers. In any case, the intent is to determine the ratio of monitored values as a gain adjustment to compensate the measurement signal for variations that occurs subsequent to the current sample. In step 1412, a decision is made to either apply or not apply the correction calculated in step 1408. The decision for applying the correction may be based upon the magnitude of the correction, timing of the process cycle or other factors. For example, if a correction is determined to be excessively large (for instance by evaluating the current correction value versus a linear model of expected correction values or a standard deviation of historical correction values), the correction may not be applied, and the process of FIG. 14 may be aborted, as the excessively large correction may be indicative of some unknown system failure or fault condition. If the correction is to be applied, the process advances to step 1416 where the correction is applied to the measurement signal. The corrected or uncorrected current measurement signal can then be evaluated to determine the state of the process (step 1418). If the process is to continue for the current wafer (step 1420), the process reverts to step 1406 and interrogates the wafer for another sample. If the process is to end for the current wafer (step 1420), the process ends.

As discussed herein, the correction is commonly referred to as a ratio or gain correction. As presented by the mathematics discussed below, the correction has been defined in terms of ratioed values of the reference and measurement signal values. This mathematical treatment is done as a matter of convenience, and it may be understood that other equivalent mathematical treatments are possible and equivalent.

Figure 15:
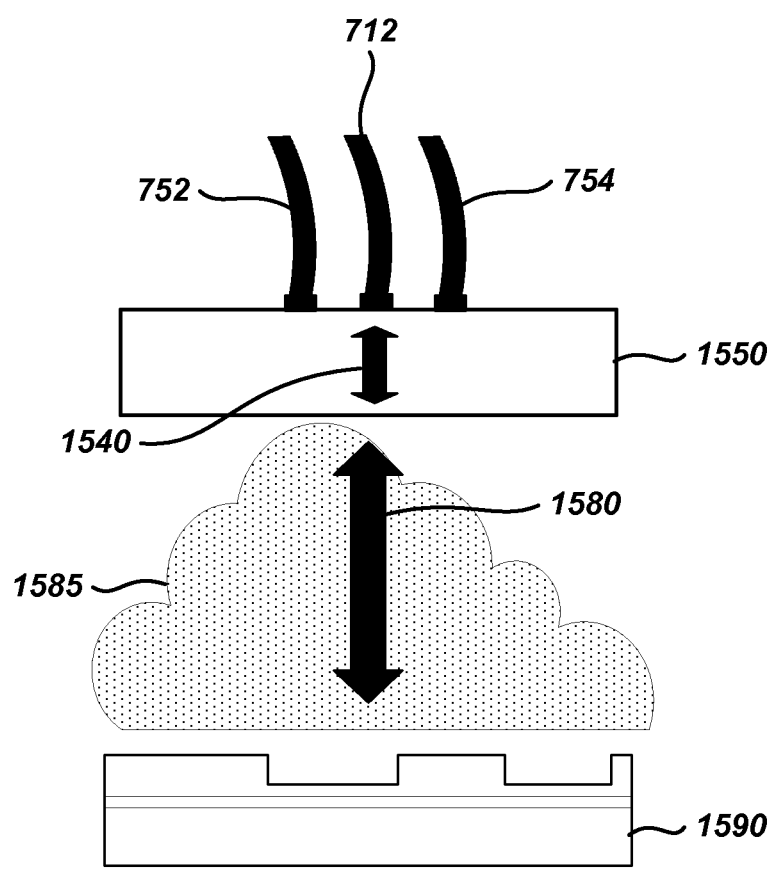
FIG. 15 is a pictorial schematic of portions of an operating environment of an optical measurement system, in accordance with an exemplary embodiment of the present invention.

FIG. 15 is a pictorial schematic of portions of the operating environment of an optical measurement system including source optical fiber assembly 712, measurement optical fiber assembly 754, reference optical fiber assembly 752, optical assembly 1550 and workpiece 1590. Although not shown, optical assembly 1550 may include sub-elements such as optical lenses, mirrors, and windows. Light signals 1540 and 1580 are both transmitted and reflected from elements of optical assembly 1550 and workpiece 1590. Light signals other than 1540 and 1580 may arise from the presence of light emitting plasma 1585, reflections from optical windows inside a process chamber (not shown) or other ambient light. Characteristics of the measurement system affecting the light signal may be defined mathematically as follows:

$F_s$=detection function of spectrograph
$I_l$=illumination intensity from source
$T_{sc}$=transmission of source fiber
$T_{ref}$=transmission of reference fiber
$T_{sig}$=transmission of signal fiber
$R_{sig}$=reflection coefficient from elements in signal path
$R_{ref}$=reflection coefficient from elements in reference path
$R_w$=reflection coefficient of a workpiece
$R_{si}$=reflection coefficient of a silicon wafer
a=workpiece reflection weighting factor for reference path
b=workpiece reflection weighting factor for signal path
$I_{pRef}$=illumination intensity from plasma or ambient, after transmission through a reference fiber, as seen through a reference path
$I_{pSig}$=illumination intensity from plasma or ambient, after transmission through a signal fiber, as seen through a signal path It should be noted that any or all of these characteristics may be wavelength, time, temperature or other factor dependant and give rise to measurement error and/or drift. Using a referenced and stabilized optical measurement system as described herein with the mathematical signal analysis discussed below may compensate for any/all of these sources of variation.

Equations for the total light signals, including source and ambient light, in the reference and signal (measurement) channels of a light analyzing device, such as a spectrograph, may be defined as follows (EQNS. 1 and 2):

$$M_{ref}(\lambda,t)=F_s I_l T_{sc} T_{ref}(R_{ref}+aR_w)+F_s I_{pRef} \qquad \text{EQN. 1}$$

$$M_{sig}(\lambda,t)=F_s I_l T_{sc} T_{sig}(R_{sig}+bR_w)+F_s I_{pSig} \qquad \text{EQN. 2}$$

It may be noted that when a≠0, in the above equation, this represents a stray light term intermingling light reflected from a workpiece into a reference signal channel. When the source light is not provided ($I_l$=0), such as by either strobing a flashlamp or alternatingly shuttering and unshuttering a continuous source, the light signals are as follows (EQNS. 3 and 4):

$$M_{ref}(\lambda,t)=F_s I_{pRef} \qquad \text{EQN. 3}$$

$$M_{sig}(\lambda,t)=F_s I_{pSig} \qquad \text{EQN. 4}$$

Subtracting these EQNS. 3 and 4 from EQNS. 1 and 2 respectively, results in a pair of difference measurements (EQNS. 5 and 6), one for each of the signal (measurement) and reference, which do not contain information about the ambient/plasma background light, but only information about light reflected within the optical assembly and from a workpiece. Measurements associated with EQNS. 1-6 may be collected/stored/processed during various steps of process 1300. For each step of process 1300, total light signals including source light and ambient/plasma light (EQNS. 1 and 2) and not including source light (EQNS. 3 and 4) may be collected.

$$M_{ref}(\lambda,t)=F_s I_l T_{sc} T_{ref}(R_{ref}+aR_w) \qquad \text{EQN. 5}$$

$$M_{sig}(\lambda,t)=F_s I_l T_{sc} T_{sig}(R_{sig}+bR_w) \qquad \text{EQN. 6}$$

When difference measurements (EQNS. 7 and 8) are collected using a non-reflective workpiece or other element, which directs light away from returning to the optical assembly ($R_w$=0), isolation of system quantities may be achieved separate from workpiece conditions. Measurements associated with EQNS. 7 and 8 may, for example, be collected/stored/processed during step 1320 of process 1300.

$$M_{ref}(\lambda,t_0)=F_s I_l T_{sc} T_{ref}(R_{ref}) \qquad \text{EQN. 7}$$

$$M_{sig}(\lambda,t_0)=F_s I_l T_{sc} T_{sig}(R_{sig}) \qquad \text{EQN. 8}$$

When difference measurements (EQNS. 9 and 10) are collected using a known reflective workpiece, such as a bare silicon wafer, isolation of system quantities may be achieved under known workpiece conditions. Measurements associated with EQNS. 9 and 10 may, for example, be collected/stored/processed during step 1330 of process 1300.

$$M_{ref}(\lambda,t_1)=F_s I_l T_{sc} T_{ref}(R_{ref}+aR_{si}) \qquad \text{EQN. 9}$$

$$M_{sig}(\lambda,t_1)=F_s I_l T_{sc} T_{sig}(R_{sig}+bR_{si}) \qquad \text{EQN. 10}$$

Taking the ratio of averages of the measurements of EQNS. 7 and 8 provides a referenced average value for a "dark" no-workpiece measurement <Dark>. Taking the ratio of averages of the measurements of EQNS. 9 and 10 provides a referenced average value for a "reference" workpiece measurement <Reference>. Taking the ratio of averages of the measurements of EQNS. 5 and 6 provides a referenced measurement for a currently monitored workpiece <M>. Combining these "dark" and "reference" measurements with current measurements of the monitored unknown workpiece, as follows, yields a referenced and stabilized measurement (EQN. 11) of $r(\lambda,t)$, the reflectivity of the current workpiece relative to the reflectivity of the known reference workpiece. Measurements associated with EQN. 11 and related mathematical processing may, for example, be collected/stored/processed during step 1340 of process 1300.

$$r(\lambda, t) = \frac{\frac{M_{sig}(\lambda, t)}{M_{ref}(\lambda, t)} - \frac{M_{sig}(\lambda, t_0)}{M_{ref}(\lambda, t_0)}}{\frac{M_{sig}(\lambda, t_1)}{M_{ref}(\lambda, t_1)} - \frac{M_{sig}(\lambda, t_0)}{M_{ref}(\lambda, t_0)}} = \frac{M - (\text{Dark})}{(\text{Reference}) - (\text{Dark})} \quad \text{EQN. 11}$$

If the effect of solarization on the transmission of the signal and reference fibers is about the same, then, $$\left(\frac{T_{sig}(\lambda, t_i)}{T_{ref}(\lambda, t_i)} \sim 1\right).$$

If the stray light is small enough to be neglected, then since, $$(\lim_{\alpha \to 0} r(\lambda, t_i)$$

EQN 11, reduces to EQN. 12. The transmission of the signal and reference branches may be made nearly equal, for example, as described herein by matching of fiber type, equal optical energy applied to both fibers and other methods. Stray light may be minimized, for example, by appropriate optical design and baffling.

$$r(\lambda, t) \cong \frac{R_w}{R_{st}} \quad \text{EQN. 12}$$

This referenced and stabilized measurement of the reflectivity of the current workpiece may be used to determine process control parameters such as film thickness or changing reflectivity via direct correlation with the value of the reflectivity or parametric modeling and/or fitting of a reflectivity curve as a function of wavelength. Measurements for determination of <Reference> and <Dark> may be collected/stored/processed prior to measurement of any workpieces or may be collected/stored/processed interleaved with measurements of any one or multiple workpieces. Furthermore, referenced measurement <M> for a currently monitored workpiece may be updated for each new measurement or may be intermittently updated as necessary to achieve a desired/predetermined level of measurement stability. Although the above mathematical analysis specifically discusses the stabilization and referencing of the optical measurement against stray light and optical fiber transmission variation; the same analysis may be performed with respect to any of the sources of measurement error, drift or variation discussed herein.

The changes described above, and others, may be made in the optical measurement systems described herein without departing from the scope hereof. For example, although certain examples are described in association with semiconductor wafer processing equipment, it may be understood that the optical measurement systems described herein may be adapted to other types of processing equipment such as roll-to-roll thin film processing, solar cell fabrication or any application where high precision optical measurement may be required. Furthermore, although certain embodiments discussed herein describe the use of a common light analyzing device, such as an imaging spectrograph; it should be understood that multiple light analyzing devices with known relative sensitivity may be utilized.

It should thus be noted that the matter contained in the above description or shown in the accompanying drawings should be interpreted as illustrative and not in a limiting sense. The following claims are intended to cover all generic and specific features described herein, as well as all statements of the scope of the present method and system, which, as a matter of language, might be said to fall there between.

The exemplary embodiments described herein were selected and described in order to best explain the principles of the invention and the practical application, and to enable others of ordinary skill in the art to understand the invention for various embodiments with various modifications as are suited to the particular use contemplated. The particular embodiments described herein are in no way intended to limit the scope of the present invention as it may be practiced in a variety of variations and environments without departing from the scope and intent of the invention. Thus, the present invention is not intended to be limited to the embodiment shown, but is to be accorded the widest scope consistent with the principles and features described herein.

The flowchart and block diagrams in the figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems which perform the specified functions or acts, or combinations of special purpose hardware and computer instructions.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

What is claimed is:

1. A referenced and stabilized optical measurement system comprising:
a non-continuous light source for generating a flash source light comprising:
a flash assembly optically coupled to said optics assembly, said flash assembly comprising:
a flashlamp for generating a flash source light;
a flash assembly housing, wherein the flashlamp is disposed at least partially within the flash source housing;
a flash assembly containment housing disposed at least partially within the flash assembly housing forming a flash assembly purge gas volume, said flash assembly purge gas volume containing at least a portion of a flash source light path from said non-continuous light source;
an inlet gas port coupled with the flash assembly containment housing; and
an exhaust gas port coupled with the flash assembly containment housing, wherein the inlet gas port and the exhaust gas port enable purging of gas from said flash assembly purge gas volume;
an optics assembly optically coupled to the non-continuous light source for receiving the flash source light, said optics assembly comprising:
an optics assembly housing;
light splitting optics disposed at least partially within the optics assembly housing for receiving the flash source light from said non-continuous light source and deriving a reference light from said flash source light and for deriving a measurement light from said flash source light;
illumination optics at least partially within the optics assembly housing for directing the measurement light to a workpiece for interrogating the workpiece; and
collecting optics at least partially within the optics assembly housing for receiving the measurement light reflected from the workpiece; and
a light analyzer assembly optically coupled to the optics assembly for independently receiving the reference light and the measurement light via separate fiber-optically coupled optical paths, said light analyzer assembly comprising:
a reference light image sensor for sensing the reference light and converting the reference light to a reference signal;
a measurement light image sensor for sensing the measurement light and converting the measurement light to a measurement signal; and
a measurement signal processor for receiving and modifying the measurement signal based on the reference signal.

2. The optical measurement system of claim 1, further comprising:
a measurement optical fiber assembly optically coupled between the optics assembly and the light analyzer assembly, the measurement optical fiber assembly comprising:
a first predetermined quantity of optical fibers, each of the predetermined quantity of optical fibers having a first end and a second end and a first predetermined length between the first and second ends, each of said predetermined quantity of optical fibers comprised of a predetermined composition; and a reference optical fiber assembly optically coupled between the optics assembly and the light analyzer assembly, the reference optical fiber assembly comprising:
a second predetermined quantity of optical fibers, wherein the second predetermined quantity is equivalent to the first predetermined quantity, each of the predetermined quantity of optical fibers having a first end and a second end and a second predetermined length between the first and second ends, wherein the second predetermined length is equivalent to the first predetermined length, each of said predetermined quantity of optical fibers comprised of the predetermined composition.

3. The optical measurement system of claim 2, wherein the optics assembly further comprises:
an optical purged volume containment housing disposed at least partially within the optics assembly housing forming a purge gas volume, said purge gas volume containing at least one of a flash source light path to said light splitting optics, a measurement light path from said light splitting optics, a reference light path from said splitting optics, a measurement light path from said collecting optics, a reference measurement light path between said light splitting optics and said reference optical fiber assembly, and a measurement light path between said collecting optics and said measurement light fiber assembly;
an inlet gas port coupled with the optical purged volume containment housing; and
an exhaust gas port coupled with the optical purged volume containment housing, wherein the inlet gas port and the exhaust gas port enable purging of gas from said purge gas volume.

4. The optical measurement system of claim 1, wherein the optics assembly further comprises:
an optical purged volume containment housing disposed at least partially within the optics assembly housing forming a purge gas volume, said purge gas volume containing at least one of a flash source light path to said light splitting optics, a measurement light path from said light splitting optics, a reference light path from said splitting optics, and a measurement light path from said collecting optics;
an inlet gas port coupled with the optical purged volume containment housing; and
an exhaust gas port coupled with the optical purged volume containment housing, wherein the inlet gas port and the exhaust gas port enable purging of gas from said purge gas volume.

5. The optical measurement system of claim 1, wherein the light analyzer assembly further comprises:
a single image sensor, said image sensor comprising:
a first image sensor portion comprising the reference light image sensor; and
a second image sensor portion comprising the measurement light image sensor.

6. The optical measurement system of claim 1, wherein the non-continuous light source is optically coupled directly to said optics assembly.

7. The optical measurement system of claim 1, wherein the flash assembly being optically coupled directly to said optics assembly.

8. The optical measurement system of claim 1, further comprises:
a source light fiber assembly optically coupled between the flash assembly and the optics assembly.

9. The optical measurement system of claim 1, wherein the light analyzer assembly further comprises:
a spectrograph; and
a computer.

10. The optical measurement system of claim 1, wherein the light analyzer assembly further comprises:
a light analyzer assembly purge gas volume containment housing forming a light analyzer purge gas volume, said light analyzer purge gas volume containing at least one of a reference light path to the reference light image sensor and a measurement light path to the measurement light image sensor;
an inlet gas port coupled with the light analyzer assembly purge gas volume containment housing; and
an exhaust gas port coupled with the light analyzer assembly purge gas volume containment housing, wherein the inlet gas port and the exhaust gas port enable purging of gas from said light analyzer assembly purge gas volume.

11. The optical measurement system of claim 1, wherein the workpiece is a semiconductor wafer.

12. The optical measurement system of claim 1, wherein the optical measurement system is integrated with a semiconductor processing tool.

13. The optical measurement system of claim 1, wherein at least one of the light source, optics assembly and light analyzing device is purgeable.

14. The optical measurement system of claim 1, wherein the non-continuous light source is one of a flashlamp and a combination of a continuous light source and a light source shuttering mechanism.

15. A method for high stability optical measurements comprising:
providing a common light source, comprising:
a flash assembly optically coupled to said optics assembly, said flash assembly comprising:
a flashlamp for generating a flash source light;
a flash assembly housing, wherein the flashlamp is disposed at least partially within the flash source housing;
a flash assembly containment housing disposed at least partially within the flash assembly housing forming a flash assembly purge gas volume, said flash assembly purge gas volume containing at least a portion of a flash source light path from said common light source;
an inlet gas port coupled with the flash assembly containment housing; and
an exhaust gas port coupled with the flash assembly containment housing, wherein the inlet gas port and the exhaust gas port enable purging of gas from said flash assembly purge gas volume;
configuring an optics assembly for receiving source light from said common light source and deriving reference light and signal light from said source light;
interrogating a workpiece with said optics assembly and subsequently directing said signal light to a common light analyzing device; and
directing said reference light and said measurement to said common light analyzing device via separate fiber-optically coupled optical paths.

16. The method of claim 15, further comprises:
wherein said high stability optical measurements are performed during semiconductor processing.

17. The method of claim 15, further comprises:
receiving a dark calibration value of a ratio of dark reference signal and a dark measurement signal derived from a dark sample;
receiving a known calibration value of a ratio of known reference signal and a known measurement signal derived from a known sample;
receiving a monitored ratio value of a ratio of monitored reference signal and a monitored measurement signal derived from a monitored workpiece sample;
detecting a current reference intensity of the reference light;
detecting a current measurement intensity of the measurement light;
determining a ratio of the current reference intensity and the current measurement intensity; and
compensating the current measurement intensity using the dark calibration value, the known calibration value, the ratio of the current reference intensity and the current measurement intensity.

18. The method of claim 17, further comprises:
evaluating a state of a process for the workpiece sample using the compensated current measurement intensity.

* * * * *